(12) United States Patent
Toftgard et al.

(10) Patent No.: US 6,448,020 B1
(45) Date of Patent: Sep. 10, 2002

(54) MOLECULES ASSOCIATED WITH THE HUMAN SUPPRESSOR OF FUSED GENE

(75) Inventors: Rune Toftgard, Satragardsvagen 209, S-127 36 Skarholmen (SE); Peter G. Zaphiropoulos, Tullinge Strand 96, S-146 54 Tullinge (SE); Priit Kogerman, Flugsvampsvagen 3, S-141 60 Huddinge (SE); Thomas Grimm, Stockholm (SE)

(73) Assignees: Rune Toftgard, Skarholmen (SE); Peter G. Zaphiropoulos, Tullinge (SE); Priit Kogerman, Tabasalu (EE)

( * ) Notice: Subject to any disclaimer, the term of this patent is extended or adjusted under 35 U.S.C. 154(b) by 0 days.

(21) Appl. No.: 09/581,831

(22) PCT Filed: Dec. 18, 1998

(86) PCT No.: PCT/SE98/02383

§ 371 (c)(1),
(2), (4) Date: Aug. 21, 2000

(87) PCT Pub. No.: WO99/32517

PCT Pub. Date: Jul. 1, 1999

(30) Foreign Application Priority Data

Dec. 19, 1997 (SE) ................................................ 9704788
Jun. 26, 1998 (SE) ................................................ 9802293

(51) Int. Cl.[7] ........................ G01N 33/53; A61K 39/39; C07K 1/00; C07K 16/00; C12P 21/08
(52) U.S. Cl. ..................... 435/7.1; 424/130.1; 530/350; 530/387.9; 530/388.1
(58) Field of Search .......................... 435/6, 91.1, 69.1, 435/455, 325; 514/2, 44; 530/300, 350, 387.1, 388.1; 536/24.5

(56) References Cited

PUBLICATIONS

Anh Pham et al., The suppressor of fused Gene Encodes a Novel PEST Protein Involved in Drosophila Segment Polarity Establishment, GENETICS, 140: (Jun. 1995) pp. 587–598.*

Donna M. Stone et al., Characterization of the human Suppressor of fused, a negative regulator of the zinc–finger transcription factor Gli, Journal of Cell Science 112, (1999) pp. 4437–4448.*

Genebank, 002493.*

Anh Pham et al., "The Suppressor of fused Gene Encodes a Novel PEST Protein Involved in Drosophila Segment Polarity Establishment," Genetics, vol. 140, Jun. 1995, pp. 587–598.

Pascal Therond et al., "Functional Domains of Fused, a Serine–Threonine Kinase Required for Signaling in Drosophila," Genetics, vol. 142, Apr. 1996, pp. 1181–1198.

Veronique Monnier et al., "Suppressor of fused links Fused Cubitus interruptus on the Hedgehog signalling pathway," Current Biology, vol. 8, No. 10, May 1998, pp. 583–586.

Thomas Preat et al., "a putative serine/threonine protein kinase encoded by the segment–polarity fused gene of Drosophila," Nature, vol. 347, Sep. 6, 1990, pp. 87–89.

* cited by examiner

*Primary Examiner*—Andrew Wang
*Assistant Examiner*—Jane Zara
(74) *Attorney, Agent, or Firm*—Young & Thompson

(57) ABSTRACT

The present invention relates to proteins, polypeptides and nucleotides related to the human homologue of the Drosophila suppressor of fused gene, which is involved in the transduction of signals in the HH-PTC pathway. The invention also relates to antibodies raised against the polypeptides according to the invention. The molecules according to the present invention are useful in diagnostic and therapeutic methods relating to conditions associated with defects in said pathway, especially certain malformations and cancer. Other fields of application of the molecules according to the invention are e.g. studies of embryonic development, gene transcription and tissue repair.

6 Claims, 8 Drawing Sheets

Figure 1A

```
  1 MAELRPSGAPGPTAPPAPGPTAPPAFASLFPPGLHAIYGECRRLYPDQPN    Human
    |||  ..  |:...:            ||||.||.:.  .:||:|||
  1 MAEANLDKKPEVKP...............PPGLKAIIDHLGQVYPNQPN    Drosophila 51 PLQVTAIVKYWLGGPDPLDYVSMYRNVGSPSANIPEHWHYISFGLSDLYG    Human
    ||||..::|||||||.|||||:|||:  .|... |:|.||||||||||.|
 35 PLQVTTLLKYWLGGQDPLDYISMYKFPGDVDRNVPPHWHYISFGLSDLHG    Drosophila 101 DNRVHEFTGTDGPSGFGFELTFRLKRETGE...........SAPPTWPAE    Human
    |:|||  .:.  ..||:||||||||| :.. |         :|||||:
 85 DERVHLREEGVTRSGMGFELTFRLAKTEIELKQQIENPEKPQRAPTWPAN    Drosophila 140 LMQGLARYVFQSENTFCSGDHVSWHSPLDNS.ESRIQHMLLTEDPQMQPV    Human
    |:|:::||.||.:|.:| ||:::.||.| .|:::|::|:..:|||:...:
135 LLQAIGRYCFQTGNGLCFGDNIPWRKSLDGSTTSKLQNLLVAQDPQLGCI    Drosophila 189 QTPFGVVTFLQIVGVCTEELHSAQQWNGQGILELLRTVPIAGGPWLITDM    Human
    :||  |.|.| |||| .:||. | .|||.|:|::||  .||.||:|:|
185 DTPTGTVDFCQIVGVFDDELEQASRWNGRGVLNFLRQDMQTGGDWLVTNM    Drosophila 239 RRGETIFEIDPHLQERVDKGIETDGSNLSGVSAKCAWDDLSRPPEDDED.    Human
    |.  .:||:  |. ..:::.:|.:||:|.||.|.  .: :|....| .|:
235 DRQMSVFELFPETLLNLQDDLEKQGSDLAGVNADFSFRELKPTKEVKEEV    Drosophila 288 .....SRSICIGTQPRRLSGKDTEQIRETLRRGLEINSKPVLPPINPQRQ    Human
         | ... :... |.|.:.: ..  .:.:..:.:.|...: ...   : |
285 DFQALSEKCANDENNRQLTDTQMKREEPSFPQSMSMSSNSLHKSCPLDFQ    Drosophila 333 NGLPHDRAPSRKDSLESDSSTAIIPHELIRTRQLESVHLKFNQESGALIP    Human
    .- |:                         . |:::.:.:..: : .:
335 AQAPN....................CISLDGIEITLAPGVAKYLL        Drosophila 383 LCLRGRLLHGRHFTYKSITGDMAITFVSTGVEGAFATEEHPYAAHGPWLQ    Human
    |.:::|: ||||||:|  ...:|:|:|..:|.|. .| :.||:. | |:|
360 LAIKDRIRHGRHFTFK..AQHLALTLVAESVTGSAVTVNEPYGVLGYWIQ    Drosophila 433 ILLTEEFVEKMLEDL..EDLTSPEEFKLPKEYSWPEKKLKVSI.LPDVVF    Human
    :|:..|:|.|.:::||  ..:|... | | |..||:|.|||  |  |:|.:
408 VLIPDELVPRLMEDFCSAGLDEKCEPKERLELEWPDKNLKLIIDQPEPVL    Drosophila 480 DSPLH......    Human
    . .|.
458 PMSLDAAPLKM    Drosophila
```

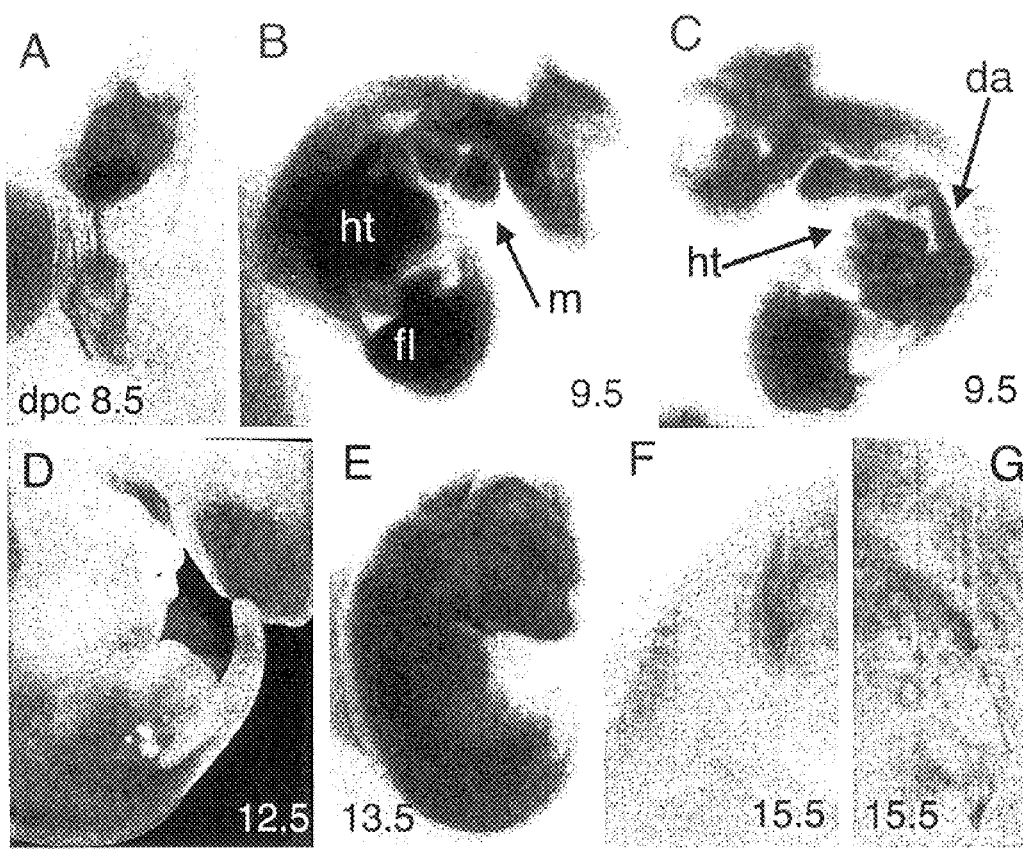

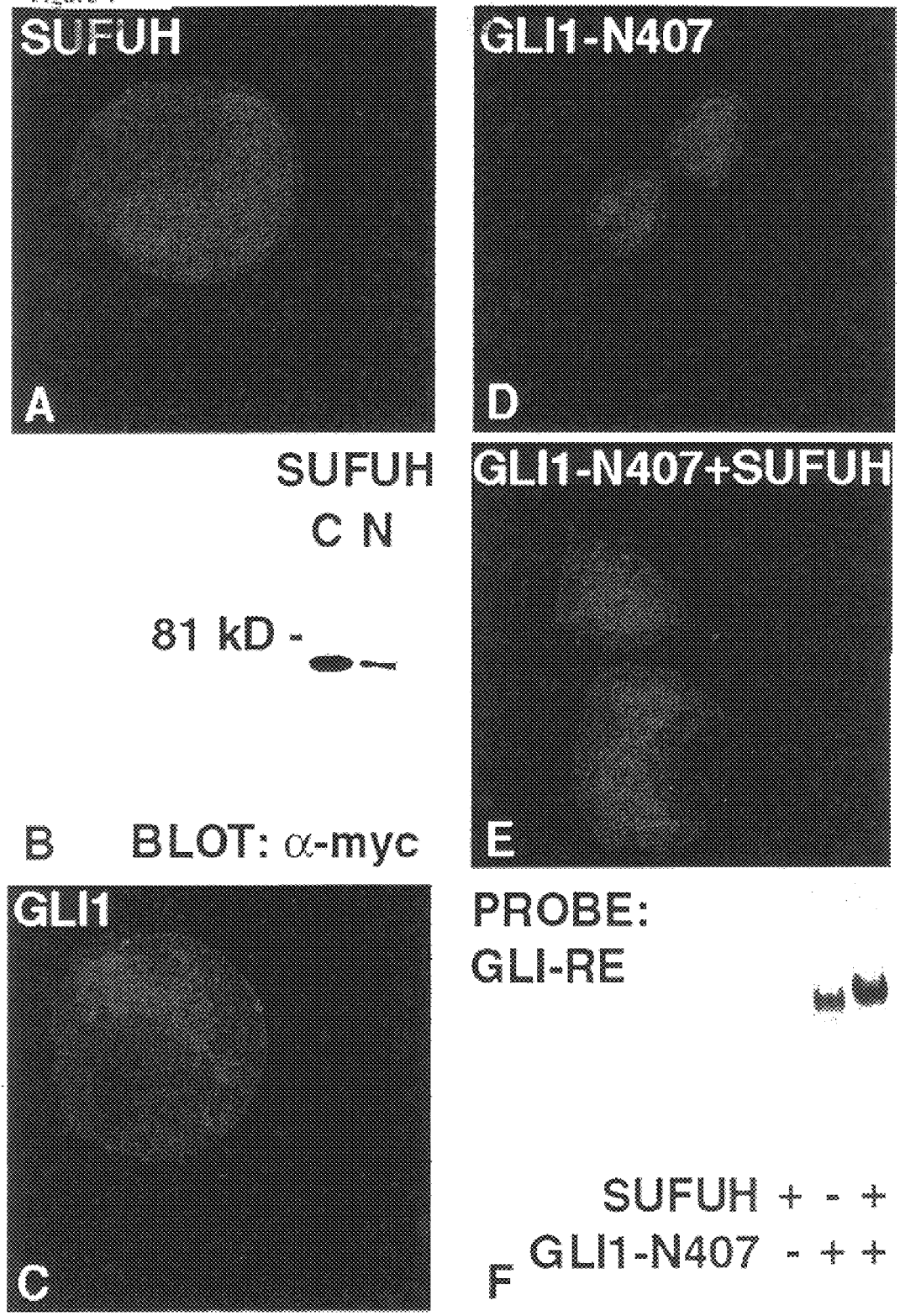

SEQUENCE LISTING

```
<160> NUMBER OF SEQ ID NOS:  5

<210> SEQ ID NO 1
<211> LENGTH: 2239
<212> TYPE: DNA
<213> ORGANISM: Homo sapiens
<220> FEATURE:
<221> NAME/KEY: CDS
<222> LOCATION: (167)..(1618)

<400> SEQUENCE: 1
gacagcctgg gcggacagtg cgccgtgcgc aggcgcggag ctagacctcg ctgcagcccc      60
catcgcctcg gggagtctca cccaccgagt ccgcccgctg gcccgtcagt gctctccccg     120
tcgtttgccc tctccagttc ccccagtgcc tgccctacgc accccg atg gcg gag       175
                                                    Met Ala Glu
                                                     1 ctg cgg cct agc ggc gcc ccc ggc ccc acc gcg ccc ccg gcc cct ggc       223
Leu Arg Pro Ser Gly Ala Pro Gly Pro Thr Ala Pro Pro Ala Pro Gly
      5                  10                  15 ccg act gcc ccc ccg gct ttc gct tcg ctc ttt ccc ccg gga ctg cac       271
Pro Thr Ala Pro Pro Ala Phe Ala Ser Leu Phe Pro Pro Gly Leu His
 20                  25                  30                  35 gcc atc tac gga gag tgc cgc cgc ctt tac cct gac cag ccg aac ccg       319
Ala Ile Tyr Gly Glu Cys Arg Arg Leu Tyr Pro Asp Gln Pro Asn Pro
                 40                  45                  50 ctc cag gtt acc gct atc gtc aag tac tgg ttg ggt ggc cca gac ccc       367
Leu Gln Val Thr Ala Ile Val Lys Tyr Trp Leu Gly Gly Pro Asp Pro
             55                  60                  65 ttg gac tat gtt agc atg tac agg aat gtg ggg agc cct tct gct aac       415
Leu Asp Tyr Val Ser Met Tyr Arg Asn Val Gly Ser Pro Ser Ala Asn
         70                  75                  80 atc ccc gag cac tgg cac tac atc agc ttc ggc ctg agt gat ctc tat       463
Ile Pro Glu His Trp His Tyr Ile Ser Phe Gly Leu Ser Asp Leu Tyr
     85                  90                  95 ggt gac aac aga gtc cat gag ttt aca gga aca gat gga cct agt ggt       511
Gly Asp Asn Arg Val His Glu Phe Thr Gly Thr Asp Gly Pro Ser Gly
100                 105                 110                 115 ttt ggc ttt gag ttg acc ttt cgt ctg aag aga gaa act ggg gag tct       559
Phe Gly Phe Glu Leu Thr Phe Arg Leu Lys Arg Glu Thr Gly Glu Ser
                120                 125                 130
```

```
gcc cca cca aca tgg ccc gca gag tta atg cag ggc ttg gca cga tac    607
Ala Pro Pro Thr Trp Pro Ala Glu Leu Met Gln Gly Leu Ala Arg Tyr
            135                 140                 145 gtg ttc cag tca gag aac acc ttc tgc agt ggg gac cat gtg tcc tgg    655
Val Phe Gln Ser Glu Asn Thr Phe Cys Ser Gly Asp His Val Ser Trp
        150                 155                 160 cac agc cct ttg gat aac agt gag tca aga att cag cac atg ctg ctg    703
His Ser Pro Leu Asp Asn Ser Glu Ser Arg Ile Gln His Met Leu Leu
    165                 170                 175 aca gag gac cca cag atg cag ccc gtg cag aca ccc ttt ggg gta gtt    751
Thr Glu Asp Pro Gln Met Gln Pro Val Gln Thr Pro Phe Gly Val Val
180                 185                 190                 195 acc ttc ctc cag atc gtt ggt gtc tgc act gaa gag cta cac tca gcc    799
Thr Phe Leu Gln Ile Val Gly Val Cys Thr Glu Glu Leu His Ser Ala
            200                 205                 210 cag cag tgg aac ggg cag ggc atc ctg gag ctg ctg cgg aca gtg cct    847
Gln Gln Trp Asn Gly Gln Gly Ile Leu Glu Leu Leu Arg Thr Val Pro
        215                 220                 225 att gct ggc ggc ccc tgg ctg ata act gac atg cgg agg gga gag acc    895
Ile Ala Gly Gly Pro Trp Leu Ile Thr Asp Met Arg Arg Gly Glu Thr
    230                 235                 240 ata ttt gag atc gat cca cac ctg caa gag aga gtt gac aaa ggc atc    943
Ile Phe Glu Ile Asp Pro His Leu Gln Glu Arg Val Asp Lys Gly Ile
245                 250                 255 gag aca gat ggc tcc aac ctg agt ggt gtc agt gcc aag tgt gcc tgg    991
Glu Thr Asp Gly Ser Asn Leu Ser Gly Val Ser Ala Lys Cys Ala Trp
260                 265                 270                 275 gat gac ctg agc cgg ccc ccc gag gat gac gag gac agc cgg agc atc   1039
Asp Asp Leu Ser Arg Pro Pro Glu Asp Asp Glu Asp Ser Arg Ser Ile
            280                 285                 290 tgc atc ggc aca cag ccc cgg cga ctc tct ggc aaa gac aca gag cag   1087
Cys Ile Gly Thr Gln Pro Arg Arg Leu Ser Gly Lys Asp Thr Glu Gln
        295                 300                 305 atc cgg gag acc ctg agg aga gga ctc gag atc aac agc aaa cct gtc   1135
Ile Arg Glu Thr Leu Arg Arg Gly Leu Glu Ile Asn Ser Lys Pro Val
    310                 315                 320 ctt cca cca atc aac cct cag cgg cag aat ggt ctc ccc cac gac cgg   1183
Leu Pro Pro Ile Asn Pro Gln Arg Gln Asn Gly Leu Pro His Asp Arg
325                 330                 335 gcc ccg agc cgc aaa gac agc ctg gaa agt gac agc tcc acg gcc atc   1231
Ala Pro Ser Arg Lys Asp Ser Leu Glu Ser Asp Ser Ser Thr Ala Ile
340                 345                 350                 355 att ccc cat gag ctg att cgc acg cgg cag ctt gag agc gta cat ctg   1279
Ile Pro His Glu Leu Ile Arg Thr Arg Gln Leu Glu Ser Val His Leu
            360                 365                 370 aaa ttc aac cag gag tcc gga gcc ctc att cct ctc tgc cta agg ggc   1327
Lys Phe Asn Gln Glu Ser Gly Ala Leu Ile Pro Leu Cys Leu Arg Gly
        375                 380                 385 agg ctc ctg cat gga cgg cac ttt aca tat aaa agt atc aca ggt gac   1375
Arg Leu Leu His Gly Arg His Phe Thr Tyr Lys Ser Ile Thr Gly Asp
    390                 395                 400 atg gcc atc acg ttt gtc tcc acg gga gtg gaa ggc gcc ttt gcc act   1423
Met Ala Ile Thr Phe Val Ser Thr Gly Val Glu Gly Ala Phe Ala Thr
405                 410                 415 gag gag cat cct tac gcg gct cat gga ccc tgg tta caa att ctg ttg   1471
Glu Glu His Pro Tyr Ala Ala His Gly Pro Trp Leu Gln Ile Leu Leu
420                 425                 430                 435 acc gaa gag ttt gta gag aaa atg ttg gag gat tta gaa gat ttg act   1519
Thr Glu Glu Phe Val Glu Lys Met Leu Glu Asp Leu Glu Asp Leu Thr
```

-continued

```
                    440                 445                 450
tct cca gag gaa ttc aaa ctt ccc aaa gag tac agc tgg cct gaa aag      1567
Ser Pro Glu Glu Phe Lys Leu Pro Lys Glu Tyr Ser Trp Pro Glu Lys
        455                 460                 465 aag ctg aag gtc tcc atc ctg cct gac gtg gtg ttc gac agt ccg cta      1615
Lys Leu Lys Val Ser Ile Leu Pro Asp Val Val Phe Asp Ser Pro Leu
        470                 475                 480 cac tagcctgggc tgggccctgc aggggccagc agggagccca gctgctcccc           1668
His agtgacttcc agtgtaacag ttgtgtcaac gagatctcca caaataaaag gacaagtgtg   1728
aggaagactg cgcagtgcca ccccgcagcc cagtggggtg ccatgcacag gccacaggcc   1788
ctccacctca cctccagctc aggggccgca ccccgccgct ggctaagcct tgtgacccat   1848
caggccagtg agtgggcaaa tgcggaccct ccctgcctgc agcctgcaca gattctggtt   1908
tgaggtttga ctctggaccc tggctgtgcc ctaggtggag acagccttt ttctaaccaa    1968 ccccctgccg cacagcccag caggagggag gcggacagcc agatgcagag ggagtggatg   2028
cacttcccag ctcatttctg gaagcctttg ctactcaagc cctctggcc gcggaacaat    2088 tcctctgatc atgtttggtt ttcttcttcc ttattttatt ttgtagaaac cgggtggtat   2148
tttattgctc tgcaaagatg tccagaagcc aagtatataa tgttttttaa acaaaataaa   2208
aaaaaaaaaa aaaaaaaaa aaggaaaaaa a                                    2239

<210> SEQ ID NO 2
<211> LENGTH: 484
<212> TYPE: PRT
<213> ORGANISM: Homo sapiens

<400> SEQUENCE: 2

Met Ala Glu Leu Arg Pro Ser Gly Ala Pro Gly Pro Thr Ala Pro Pro
 1               5                  10                  15

Ala Pro Gly Pro Thr Ala Pro Pro Ala Phe Ala Ser Leu Phe Pro Pro
                20                  25                  30

Gly Leu His Ala Ile Tyr Gly Glu Cys Arg Arg Leu Tyr Pro Asp Gln
            35                  40                  45

Pro Asn Pro Leu Gln Val Thr Ala Ile Val Lys Tyr Trp Leu Gly Gly
        50                  55                  60

Pro Asp Pro Leu Asp Tyr Val Ser Met Tyr Arg Asn Val Gly Ser Pro
 65                  70                  75                  80

Ser Ala Asn Ile Pro Glu His Trp His Tyr Ile Ser Phe Gly Leu Ser
                85                  90                  95

Asp Leu Tyr Gly Asp Asn Arg Val His Glu Phe Thr Gly Thr Asp Gly
            100                 105                 110

Pro Ser Gly Phe Gly Phe Glu Leu Thr Phe Arg Leu Lys Arg Glu Thr
        115                 120                 125

Gly Glu Ser Ala Pro Pro Thr Trp Pro Ala Glu Leu Met Gln Gly Leu
    130                 135                 140

Ala Arg Tyr Val Phe Gln Ser Glu Asn Thr Phe Cys Ser Gly Asp His
145                 150                 155                 160

Val Ser Trp His Ser Pro Leu Asp Asn Ser Glu Ser Arg Ile Gln His
                165                 170                 175

Met Leu Leu Thr Glu Asp Pro Gln Met Gln Pro Val Gln Thr Pro Phe
            180                 185                 190

Gly Val Val Thr Phe Leu Gln Ile Val Gly Val Cys Thr Glu Glu Leu
        195                 200                 205
```

-continued

```
His Ser Ala Gln Gln Trp Asn Gly Gln Gly Ile Leu Glu Leu Leu Arg
    210                 215                 220
Thr Val Pro Ile Ala Gly Gly Pro Trp Leu Ile Thr Asp Met Arg Arg
225                 230                 235                 240
Gly Glu Thr Ile Phe Glu Ile Asp Pro His Leu Gln Glu Arg Val Asp
                245                 250                 255
Lys Gly Ile Glu Thr Asp Gly Ser Asn Leu Ser Gly Val Ser Ala Lys
            260                 265                 270
Cys Ala Trp Asp Asp Leu Ser Arg Pro Glu Asp Asp Glu Asp Ser
        275                 280                 285
Arg Ser Ile Cys Ile Gly Thr Gln Pro Arg Arg Leu Ser Gly Lys Asp
    290                 295                 300
Thr Glu Gln Ile Arg Glu Thr Leu Arg Arg Gly Leu Glu Ile Asn Ser
305                 310                 315                 320
Lys Pro Val Leu Pro Pro Ile Asn Pro Gln Arg Gln Asn Gly Leu Pro
                325                 330                 335
His Asp Arg Ala Pro Ser Arg Lys Asp Ser Leu Glu Ser Asp Ser Ser
            340                 345                 350
Thr Ala Ile Ile Pro His Glu Leu Ile Arg Thr Arg Gln Leu Glu Ser
        355                 360                 365
Val His Leu Lys Phe Asn Gln Glu Ser Gly Ala Leu Ile Pro Leu Cys
    370                 375                 380
Leu Arg Gly Arg Leu Leu His Gly Arg His Phe Thr Tyr Lys Ser Ile
385                 390                 395                 400
Thr Gly Asp Met Ala Ile Thr Phe Val Ser Thr Gly Val Glu Gly Ala
                405                 410                 415
Phe Ala Thr Glu Glu His Pro Tyr Ala Ala His Gly Pro Trp Leu Gln
            420                 425                 430
Ile Leu Leu Thr Glu Glu Phe Val Glu Lys Met Leu Glu Asp Leu Glu
        435                 440                 445
Asp Leu Thr Ser Pro Glu Glu Phe Lys Leu Pro Lys Glu Tyr Ser Trp
    450                 455                 460
Pro Glu Lys Lys Leu Lys Val Ser Ile Leu Pro Asp Val Val Phe Asp
465                 470                 475                 480
Ser Pro Leu His

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 3
gaagctgatg tactgccagt g                                              21

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 4
gcgtcgacct ggagcgggtt cggctggt                                       28
```

```
<210> SEQ ID NO 5
<211> LENGTH: 468
<212> TYPE: PRT
<213> ORGANISM: Drosophila melanogaster

<400> SEQUENCE: 5

Met Ala Glu Ala Asn Leu Asp Lys Lys Pro Glu Val Lys Pro Pro Pro
 1               5                  10                  15

Gly Leu Lys Ala Ile Ile Asp His Leu Gly Gln Val Tyr Pro Asn Gln
             20                  25                  30

Pro Asn Pro Leu Gln Val Thr Thr Leu Leu Lys Tyr Trp Leu Gly Gly
         35                  40                  45

Gln Asp Pro Leu Asp Tyr Ile Ser Met Tyr Lys Phe Pro Gly Asp Val
     50                  55                  60

Asp Arg Asn Val Pro Pro His Trp His Tyr Ile Ser Phe Gly Leu Ser
 65                  70                  75                  80

Asp Leu His Gly Asp Glu Arg Val His Leu Arg Glu Glu Gly Val Thr
                 85                  90                  95

Arg Ser Gly Met Gly Phe Glu Leu Thr Phe Arg Leu Ala Lys Thr Glu
            100                 105                 110

Ile Glu Leu Lys Gln Gln Ile Glu Asn Pro Glu Lys Pro Gln Arg Ala
        115                 120                 125

Pro Thr Trp Pro Ala Asn Leu Leu Gln Ala Ile Gly Arg Tyr Cys Phe
    130                 135                 140

Gln Thr Gly Asn Gly Leu Cys Phe Gly Asp Asn Ile Pro Trp Arg Lys
145                 150                 155                 160

Ser Leu Asp Gly Ser Thr Thr Ser Lys Leu Gln Asn Leu Leu Val Ala
                165                 170                 175

Gln Asp Pro Gln Leu Gly Cys Ile Asp Thr Pro Thr Gly Thr Val Asp
            180                 185                 190

Phe Cys Gln Ile Val Gly Val Phe Asp Asp Glu Leu Glu Gln Ala Ser
        195                 200                 205

Arg Trp Asn Gly Arg Gly Val Leu Asn Phe Leu Arg Gln Asp Met Gln
    210                 215                 220

Thr Gly Gly Asp Trp Leu Val Thr Asn Met Asp Arg Gln Met Ser Val
225                 230                 235                 240

Phe Glu Leu Phe Pro Glu Thr Leu Leu Asn Leu Gln Asp Asp Leu Glu
                245                 250                 255

Lys Gln Gly Ser Asp Leu Ala Gly Val Asn Ala Asp Phe Ser Phe Arg
            260                 265                 270

Glu Leu Lys Pro Thr Lys Glu Val Lys Glu Glu Val Asp Phe Gln Ala
        275                 280                 285

Leu Ser Glu Lys Cys Ala Asn Asp Glu Asn Asn Arg Gln Leu Thr Asp
    290                 295                 300

Thr Gln Met Lys Arg Glu Pro Ser Phe Pro Gln Ser Met Ser Met
305                 310                 315                 320

Ser Ser Asn Ser Leu His Lys Ser Cys Pro Leu Asp Phe Gln Ala Gln
                325                 330                 335

Ala Pro Asn Cys Ile Ser Leu Asp Gly Ile Glu Ile Thr Leu Ala Pro
            340                 345                 350

Gly Val Ala Lys Tyr Leu Leu Leu Ala Ile Lys Asp Arg Ile Arg His
        355                 360                 365

Gly Arg His Phe Thr Phe Lys Ala Gln His Leu Ala Leu Thr Leu Val
    370                 375                 380
```

-continued

```
Ala Glu Ser Val Thr Gly Ser Ala Val Thr Val Asn Glu Pro Tyr Gly
385                 390                 395                 400

Val Leu Gly Tyr Trp Ile Gln Val Leu Ile Pro Asp Glu Leu Val Pro
            405                 410                 415

Arg Leu Met Glu Asp Phe Cys Ser Ala Gly Leu Asp Glu Lys Cys Glu
            420                 425                 430

Pro Lys Glu Arg Leu Glu Leu Glu Trp Pro Asp Lys Asn Leu Lys Leu
        435                 440                 445

Ile Ile Asp Gln Pro Glu Pro Val Leu Pro Met Ser Leu Asp Ala Ala
    450                 455                 460

Pro Leu Lys Met
465
```

MOLECULES ASSOCIATED WITH THE HUMAN SUPPRESSOR OF FUSED GENE

TECHNICAL FIELD

The present invention relates to novel molecules, such as proteins, polypeptides and nucleotides, involved in the transduction of signals in the hedgehog-patched (HH-PTC) pathway which takes place during the development of the cells of a human body. The invention also relates to certain advantageous uses of the molecules according to the invention in therapy and diagnosis.

BACKGROUND

In the study of the development of cells, fruit flies have extensively been used as a model, as they are less complex than mammalian cells.

Pattern formation takes place through a series of logical steps, reiterated many times during the development of an organism. Viewed from a broader evolutionary perspective, across species, the same soil of reiterative pattern formations are seen. The central dogma of pattern formation has been described (Lawrence and Struhl, 1996). Three interlocking and overlapping steps are defined. Firstly, positional information in the form of morphogen gradients allocate cells into non-overlapping sets, each set founding a compartment. Secondly, each of these compartments acquire a genetic address, as a result of the function of active "selector" genes, that specify cell fate within a compartment and also instruct cells and their descendents how to communicate with cells in neighboring compartments. The third step involves interactions between cells in adjacent compartments, initiating new morphogen gradients, which directly organize the pattern.

Taking these steps in greater detail, one finds the first step in patterning to be the definition of sets of cells in each primordium. Cells are allocated according to their positions with respect to both dorsoventral and anterior/posterior axes by morphogen gradients. Allocation of cells in the dorsoventral axis constitutes the germ layers, such as mesoderm or neurectoderm.

In segmentation, the second step (the specification of cell fate in each compartment) is carried out by the gene engrailed and elements of the bithorax complex. Engrailed defines anterior and posterior compartments both in segmentation and in limb specification.

The third step in pattern formation, secretion of morphogens, functions to differentiate patterns within compartments (and thereby establish segment polarity). Initially, all cells within a compartment are equipotent, but they become diversified to form pattern. Pattern formation depends on gradients of morphogens, gradients initiated along compartment boundaries. Such gradients are established by a short-range signal induced in all the cells of the compartment in which the above mentioned selector gene engrailed is active. For segment polarity, this signal is Hedgehog. In the adjacent compartment the selector gene is inactive, ensuring that the cells are sensitive to the signal. The Hedgehog signal range is probably only a few rows of cells wide; responding cells become a linear source of a long-range morphogen, that diffuses outward in all directions. There are three known Hedgehogs, Sonic (SHH), Indian (IHH) and Desert (DHH). The proteins they encode can substitute for each other, but in wildtype animals, their distinct distributions result in unique activities. SHH controls the polarity of limb growth, directs the development of neurons in the ventral neural tube and patterns somites. IHH controls endochondral bone development and DHH is necessary for spermiogenesis. Vertebrate hedgehog genes are expressed in many other tissues, including the peripheral nervous system, brain, lung, liver, kidney, tooth primordia, genitalia and hindgut and foregut endoderm.

Thus, segment polarity genes have been identified in flies as mutations, which change the pattern of structures of the body segments. Mutations in these genes cause animals to develop the changed patterns on the surfaces of body segments, the changes affecting the pattern along the head to tail axis. For example, mutations in the gene patched cause each body segment to develop without the normal structures in the center of each segment. Instead there is a mirror or image of the pattern normally found in the anterior segment. Thus, cells in the center of the segment make the wrong structures, and point them in the wrong direction with reference to the over all head-to-tail polarity of the animal.

About sixteen genes in the class are known. The encoded proteins include kinases, transcription factors, a cell junction protein, two secreted proteins called wingless (WG) and the above mentioned Hedgehog (HH), a single transmembrane protein called patched (PTC) and some novel proteins not related to any known protein. All of these proteins are beleived to work together in signaling pathways that inform cells about their neighbors in order to set cell fates and polarities.

PTC has been proposed as a receptor for HH protein based on genetic experiments in flies. A model for the relationship is that PTC acts through a largely unknown pathway to inactivate both its own transcription and the transcription of the wingless segment polarity gene. This model proposes that HH protein, secreted from adjacent cells, binds to the PTC receptor, inactivates it and thereby prevents PTC from turning off its own transcription or that of wingless. A number of experiments have shown coordinate events between PTC and HH.

WO 96/11260 discloses the isolation of patched genes and the use of the PTC protein to identify ligands, other than the established ligand Hedgehog, that bind thereto. However, even though it is briefly suggested that drugs may be identified which can prevent the transduction of signals by the PTC protein, there are no teachings as regards how such signals are transduced.

In order to elucidate how the Hedgehog elecits signal transduction, a large complex containing the kinesin-related protein costa 12 has been proposed (Robbins et al; Cell: Jul. 25, 1997, 90(2), p. 225–34). Said complex includes the products of at least three genes: fused (a protein-serine/threonine kinase), cubitus interruptus (a transcription factor) and costal2 (a kinesin-like protein). It is concluded that in Drosophila, the complex may facilitate signaling from HH by governing access of the cubitus interruptus protein to the nucleus.

Therond et al have also studied signaling from Hedgehog in Drosophlila (Proc. Natl.Acad. Sci. USA, Apr. 30, 1996, 93(9), p. 4224–8). The Drosophila gene fused (fu) encodes a serine/threonine-protein kinase that genetic experiments have implicated in signaling initiated by hedgehog. It is proposed that the fused protein is phosphorylated during the course of Drosophila embryogenesis, as a result of hedgehog activity. As a conclusion, this reference suggests, that a reconstruction of signaling from hedgehog in cell culture should provide further access to the mechanisms by which the hedgehogs acts.

The gene encoding a suppressor of the mutant phenotype of the above discussed fused gene, denoted suppressor of fused (SUFU), has been studied in Drosophila and mice. It has been shown by mRNA levels analysed by in situ hybridisation that during mouse embryogenesis, the mouse suppressor of fixed (MSUFU) is expressed. This occurs in a specific pattern on top of a wide spread basal level including several tissues; at specific sites during limb development, in developing lung, genital area, skeletal development in somites and ribs, etc. The expression pattern is similar to the mouse patched gene (MPTC) and is compatible with a role for MSUFU in the HH-MPTC, such as SHH-PTC, signaling pathway. Thus, even though the gene suppressor of fused (SUFU) has been identified in Drosophila and studied in mice, it has not been isolated from human beings before. The prior art teachings about the interactions between the hedgehog ligand and the patched receptor in mammals is not at all sufficient for practical applications in regard of human beings. Firstly, there is a need of a better understanding of how the signals are actually elicited and transduced in said pathway. Secondly, the human homologues of the genes implicated in this pathway must also be isolated, and the cDNA thereof identified, in order to enable recombinant reproduction thereof. However, due to the substantial genetic differences between fruit flies and human beings and the complex nature of the human genome, the isolation of the human homologues to genes identified in the fruit flie is in no way a straightforward task.

SUMMARY OF THE INVENTION

The present invention fulfill the above defined need by providing novel human homologues to molecules associated with the Drosophila suppressor fused (SUFU) gene and implicated in the transduction of the signals elicited by the interaction between the patched receptor (PTC, sometimes denoted the NBCCS gene) and any one of the hedgehog ligands, e.g. the sonic hedgehog (SHH). The molecules according to the invention are nucleic acids as well as polypeptides and proteins encoded thereof, which are useful within several fields, including the study of different conditions, such as cancer and development of cancer therapies, hereditary malformation syndromes the regulation of gene transcription, studies of embryonic development, tissue repair etc. These applications will be discussed in more detail below.

The proposed research will give important basic understanding of a singaling pathway that is central to normal development and often disrupten in disease. The new knowledge will also be of great value when considering new therapeutic strategies involving modification of SHH-PTCH singaling. Potential areas include tissue repair/wound healing (brain, bone, cartilage, skin), neurodegenerative disease, testicular function and cancer. We also foresee a use of the SU(FU)H gene/protein as a diagnostic tool.

Recently, the present inventors have shown that SU(FU) co-localizes with alpha-tubulin in human cells, whereby it is associated with microtubuli similar to FU and cos2 in Drosophila.

The novel SUFU gene according to the present invention encodes a protein which is expressed in all adult tissues tested by the inventors. However, during embryonic development, it has a very restricted expression pattern, which partially overlaps with the expression of other members of the hedgehog signalling pathway and tendentially congrues with the expression of the Ci-homolog Gli-3 rather than Gli-1. In reporter gene assays, SUFU according to the invention was shown to downregulate Gli-1 induced expression.

BRIEF DESCRIPTION OF THE DRAWINGS

FIGS. 1A–1B shows a comparison of the amino acid sequence encoded by the suppressor of fused gene according to the invention with the Drosophila melanogaster sequence, while FIG. 1B illustrates the expression of the gene according to the invention in human adult tissue.

FIGS. 2A–2J illustrates expression of human suppressor of fused in mouse embryo.

FIGS. 4A–4F shows that the human suppressor of fused is localized to the cytoplasm and to the nucleus.

DETAILED DESCRIPTION OF THE INVENTION

Figure 1B:
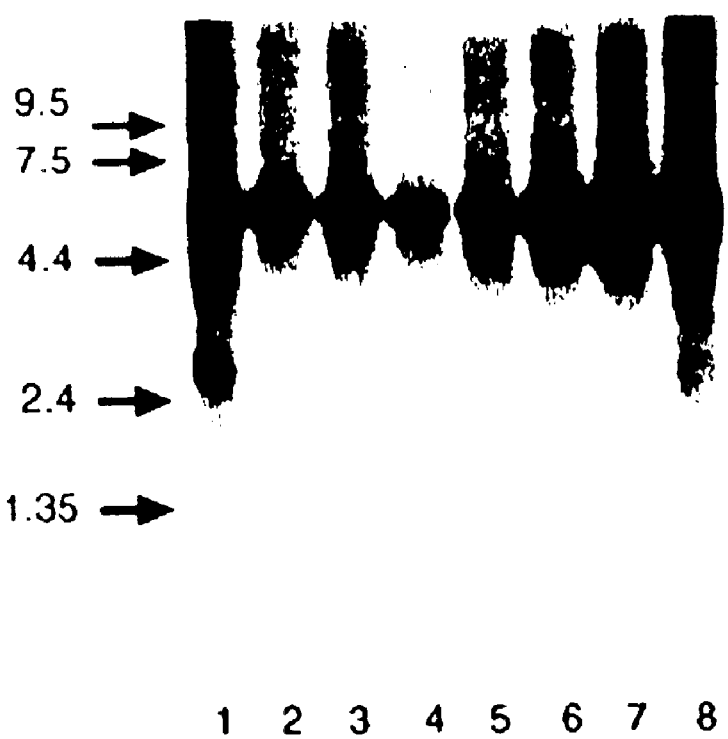

The present invention is closely linked to another invention, wherein it is observed that a human homologue of Drosophila fused is an intracellular transducer of the signal elicited at the cell membrane by interaction of ligands, such as sonic hedgehog (SHH), indian hedgehog (IHH) and desert hedgehog (DHH), with the receptor human homologue of Drosophila patched (PTC). This interaction leads to initiation of a signaling pathway by allowing PTC or its coreceptor, human homologue of Drosophila smoothened (SMOH), to activate intracellular signal transducers. A human homologue of Drosophila fused, FUH, has also been isolated by the present inventors. As mentioned above, in Drosophila cells, fused interacts with the microtubule associated protein costal-2 (cos-2) and the transcription factor cubitus interruptus (ci). The latter has human homologues denoted GLI 1-3.

Accordingly, in a first aspect, the present invention relates to a protein molecule capable of being involved in eliciting intracellular signaling in (he human HH-PTC pathway, such as the SHH-PTC pathway. More specifically, said involvement resides in a regulatory action apposing that of HH and fused. The interaction between the proteins and/or the polypeptides according to the invention is not yet fully understood. However, functional assays based on cotransfection of an expression vector for SUFUH and a reporter gene construct containing the human 5' promoter region from PTCH linked to the luciferase reporter gene have been performed in human 293 cells. The results show that SUFUH inhibits transcriptional activation of the PTCH promoter induced by GL1. Since activation of the PTCH gene transcription is a signal response in the SHH-PTCH pathway, these data strongly support the role of the SUFUH according to the present invention in this pathway. In humans, the protein molecules according to the present invention are fully or in part encoded by the human gene suppressor of fused (SUFUH). The complete sequence of the expression product of said SUFUH, which has been sequenced for the first time in accordance with the present invention, is disclosed in the Sequence Listing below and is denoted SEQ ID NO 2.

Accordingly, the protein according to the invention preferably exhibits a substantial similarity with the sequence disclosed in SEQ ID NO 2 of the Sequence Listing shown below. In a particular embodiment, the protein according to the invention is comprised of about 80% of said sequence and in a specific embodiment, it is comprised of substantially all of said amino acid sequence. However, it should probably include at least about 60% of said sequence in order to exhibit the advantageous capability of participating in the HH-PTC pathway in human beings. As someone skilled in this area easily realises, the percentages given herein will depend on possible further added fragments or sequence parts, as a protein which comprises 80% of the sequence according to SEQ ID NO 2, to which a further fragment has been added, naturally in itself will include a smaller percentage of the sequence according to this invention. Therefore, it is to be understood that any protein including the herein given percentages of SEQ ID NO 2 as disclosed are within the scope of the present invention. Further, analogues of, and functional equivalents to, the suppressor of fused proteins according to the invention are also encompassed by the present invention.

In a second aspect, the present invention relates to polypeptides comprised of suitable fragments or parts of the amino acid sequence of the above described protein. Thus, such a polypeptide is associated with the HH-PTC pathway as disclosed above and it is comprised of a subsequence of up to about 20, such as 8–15, preferably 9–12 and most preferred 10, contiguous amino acids of the sequence disclosed in SEQ ID NO 2 or conservative substitutions of said sequence. The suppressor of fused polypeptides according to the invention may be encoded by a nucleic acid amplified from genomic DNA or RNA using appropriate primers which the skilled man in this field easily chooses. In a specific embodiment, the polypeptide according to the invention is presented as an antigen, which elicits the production of an antibody which specifically binds to a polypeptide encoded by a nucleic acid according to SEQ ID NO 1, and said polypeptide does not bind to antisera raised against a polypeptide encoded by a nucleic acid sequence according to SEQ ID NO 1, which has been fully immunosorbed with a polypeptide encoded by a sequence of SEQ ID NO 2.

In a third aspect, the present invention relates to a nucleic acid encoding any one of the above defined proteins or polypeptides according to the invention. In a preferred embodiment, the nucleic acid according to the invention is such a DNA sequence as disclosed in SEQ ID NO 1. Thus, according to the present invention, for the first time, the human homologue of the Drosophila suppressor of fused gene has been isolated, the cDNA thereof has been established, sequenced and cloned. The complete cDNA sequence thereof is disclosed in SEQ ID NO 1 of the present application. The present invention also encompasses nucleotides that hybridises to part or all of the sequence of SEQ ID NO 1 as well as nucleotides hybridising to the DNA encoding the proteins and polypeptides according to the invention. Such nucleotides may e.g. be RNA sequences.

The isolated human homologue of suppressor of fused according to the invention exhibits an amino acid identity with Drosophila suppressor of fused of about 38.5%, while the amino acid similarity is about 60.0%. According to the present invention, it has been shown that in adult humans, SUFUH is widely expressed, which is based on Northern analysis (wherein the mRNA is detected), and positive tissues include epidermis, heart, brain, placenta, lung, liver, skeletal muscle, kidney and pancreas. Two messages of approximate sizes of 2.7 and 5.5 kb respectively have been detected.

SUFUH has been localized using radiation hybrid mapping to chromosome 10q24 very close to the marker AFM183XB12. This region is frequently lost in several tumor types, including melanoma, squamous cell cancer of the skin, carcionomas of the glioblastoma and neuroblastoma. Thus, SUFUH is a candidate for a tumor suppressor gene localized in this region and may play a role in the development of the above mentioned tumor types. SUFUH also maps in the candidate region for the malformation syndrome denoted "Split hand/Split foot Malformation Type 3" (SHFM3) and based on its involvement in a signaling pathway known to regulate limb development and its demonstrated expression during mouse limb development, SUFUH is a very strong candidate for the SHFM3 gene. A similar defect in development is seen in the mouse" Dactylaplasia mutant, which has been mapped to mouse chromosome 19 in an area syntenic to human 10q24 making MSUFU a strong candidate for the Dac-gene. Other genetic syndromes mapped to the genomic region including SUFUH are Partial Epilepsy, Urofacial (Ochoa) Syndrome and Spinocerebellar Ataxia.

In a fourth aspect, the present invention relates to a vector comprising a nucleic acid according to the invention, such as part of, or all of, the DNA sequence disclosed in SEQ ID NO 1. The vector preferably includes the above described nucleic acid operably linked, i.e. under the control of, a promoter, which is either constitutive or inducible. The vector can also include suitable initiation and termination codons.

In addition, the invention also relates to an expression cassette comprising any one of the nucleic acids according to the invention. Thus, one further aspect of the invention is a cell comprising an expression cassette according to the invention.

In one further aspect, the invention relates to an antibody which specifically binds to such a polypeptide as defined above, which preferably comprises at least about 10, more preferably at least 20, 40 or 50 and most preferably at least 100 or 200, or even 400 amino acids. In a specific embodiment, the antibody binds to a protein comprised of essentially all of the sequence disclosed in SEQ ID NO 2. The antibody is polyclonal or monoclonal, preferably, it is a monoclonal antibody. It can be humanized or human. Thus, the invention also relates to a cell, such as a recombinant cell, e.g. hybridomas or triomas, expressing such an antibody as defined above. The invention also relates to the use of such an antibody as a medicament or in the manufacture of a specific drug or therapy.

Thus, another aspect of the invention is a pharmaceutical composition which comprises a molecule selected from the group consisting of a vector encoding a polypeptide according to the invention or any subsequence thereof, a polypeptide according to the invention or a subsequence thereof and an antibody raised against the present polypeptides together with a pharmaceutically acceptable carrier.

Yet another aspect of the invention is a kit for detection of a human suppressor of fused gene, which kit comprises a nucleic acid sequence capable of hybridising to an essential part of the sequence disclosed in SEQ ID NO 1, preferably under stringent conditions. The invention also relates to a kit for detection of a protein encoded by a human suppressor of fused gene according to the present invention, comprising a container containing such an antibody as defined above.

In a last aspect, the invention also relates to methods for detecting any deviations from a normal human suppressor of fused gene. The method includes the steps of a) providing a biological sample of the organism and b) detecting a human suppressor of fused gene or gene product in the sample. The provision of a biological sample and detection methods will be described below in the section "Experimental".

The invention also relates to diagnostic and prognostic methods wherein mutations in pathway components are detected as well as to kits for performing such methods.

Finally, the present invention also relates to methods of treatment, wherein the above defined molecules according to the invention are used. Conditions that may be contemplated include cancers, such as basal cell cancer of the skin, medulloblastomas, trichoepitheliomas and breast cancer, conditions caused by defects in brain development, lung development, tooth and hair development and sperm formation, and tissue repair. Most preferably, the present molecules are used to diagnose, prevent and/or treat the malformation syndrome "Split hand/Split foot malformation Type 3" (SHFM3). The present molecules are also useful in gene therapy. The methods according to the invention can involve transfecting cells of a mammal with a vector expressing a polypeptide or antibody according to the invention. The transfection can be in vivo or ex vivo. Ex vivo transfection is suitably followed by re-infusing the cells into the organism. Other methods involve administering to the mammal, e.g. a human, of a therapeutically effective dose of a composition comprising a polypeptide according to the invention and a pharmacological excipient and/or carrier.

DETAILED DESCRIPTION OF THE DRAWINGS

FIG. 1A., shows the predicted amino acid sequence encoded by the SUFUH gene according to the invention (upper lines) is 40% identical with the *Drosophila melanogaster* sequence (lower lines). In the human sequence the amino terminus protein consists of a series of 20 short (A, G, P) and short hydroxylated (S, T) amino acids only (aa 6–25), including a duplicated PGPTAPPA motif, which is not found in the fly sequence. Amino acid 31–124 and amino acid 133–151 are highly conserved between human and fly. The carboxy terminal region however has a much lower similarity. A PEST motif in the Drosophila sequence (aa 308–327) which has been detected by Pham et al. is not conserved in the human sequence. 1B. Expression of SUFUH in adult human tissues. Northern Blots were performed with a fragment corresponding to bp 1182–1630 of the human cDNA as probe. The lanes are heart (1), brain (2), placenta (3), lung (4), liver (5), skeletal muscle (6) kidney (7), pancreas (8).

FIGS. 2A–K shows SUFUH expression in the mouse embryo. Whole mount in situ hybridization of NMRI mouse embryos with a murine SUFUH-specific probe at dpc 8.5–15.5.2A. Dpc 8.5, dorsal view. The somites and the neutral tube are stained. B, C. Dpc 9.5 lateral (2B) and sagital (2C) view. Additionally to the neutral tube and the developing brain structures (2C) and the somites (2B), the forelimb (fl), the mandibular arch (m) and the neighbouring hyoid arch, the heart (ht), and the dorsal aorta (da) with the dorsally extending intersegmentary arteries are stained. 2D, E. Dpc 12.5 (2D) and dpc 13.5 (2E), lateral view. The interfollicular tissue of the vibrissae field, the vertebral column and the interdigital mesenchytne are stained. F-I. Dpc 15.5. The mesenchyme between the ribs (2F, sagital view, the heart being removed), the mesenchyme underlying the tracheal epithelium (2G, sagital view) and the tongue (2H, sagital view) are stained. The interfollicular epithelium of the vibrissae field is not stained except a small area at the tip of the snout. Instead, now the follicles of the vibrissae are stained (2I, lateral view). 2J, K. Hindlimb at dpc 14.5 (2J) and 15.5 (2K), lateral view. The staining is adjacent to the chondrification zones of the arising bones.

Figure 3A:
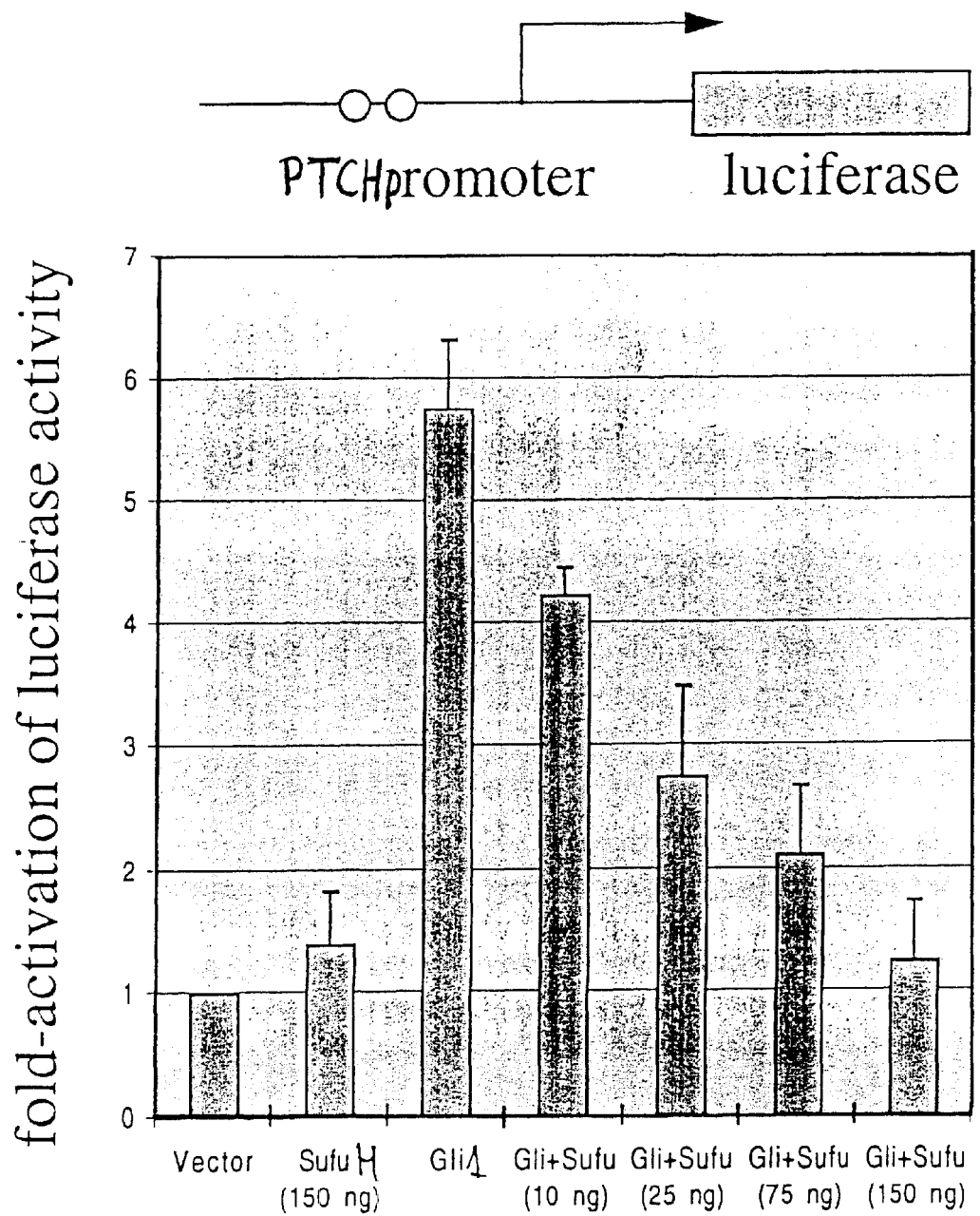
FIGS. 3A–3C shows how the human suppressor of fused inhibits transcriptional activity.
Figure 3B:
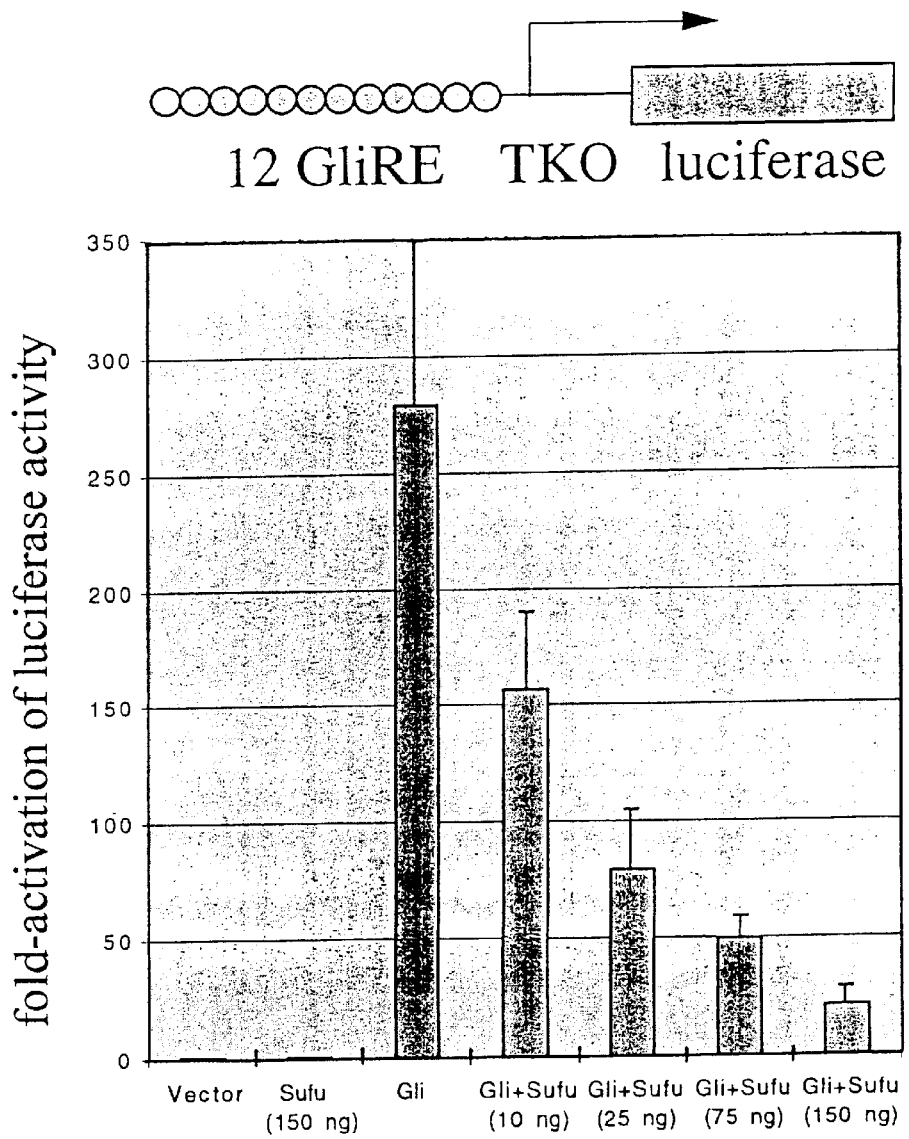
Figure 3C:
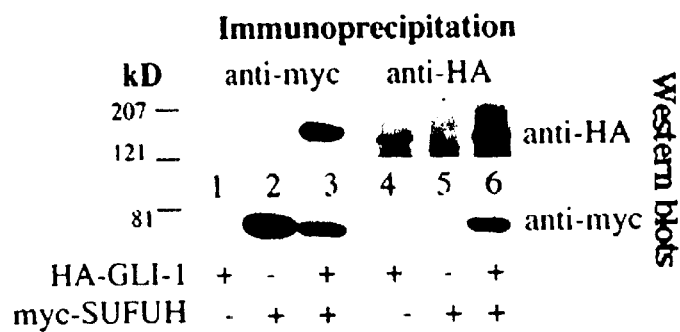

FIGS. 3A–B. shows how SUFUH inhibits GLI-1 transcriptional activity and they are in the same macromolecular complex. 293 cells were transiently transfected with a reporter construct and/or with expression constructs for SUFUH and GLI-1. 3A. The reporter was PTCH promoter connected to the luciferase marker gene. SUFUH expression has no effect on this construct whereas expressing GLI-1 results in 5–6 fold increase in luciferase activity. This activation can be inhibited by cotransfection with SUFUH in a dose-dependent manner. 3B. This experiment was similar to A except that the reporter construct was a synthetic enhancer consisting of 12 copies of the GLI consensus site linked to the Thymidine Kinase basal promoter and luciferase marker gene. The results are qualitatively the same as obtained with the PTCH promoter except that GLI-1 activates this construct much more potently (200–300-fold). 3C. SUFUH and GLI-1 coprecipitate.

The expression constructs used in this experiment were epitope-tagged (SUFUH with myc epitope and GLI-1 with HA-epitope) and transfected with these constructs as indicated. On the left-hand side is an immunoprecitation using anti-myc antibody. Myc antibody does not bring down HA-tagged gli when only HA-Gli (lane 1) or myc-sufu (lane 2) is expressed in the cells. However, myc antibody readily brings down HA-gli in cells cotransfected with both constructs (lane 3). On the right-hand panel the converse experiment is depicted. Myc-sufu is not present in anti-HA precipitates from cells transfected with HA-Gli (lane 4) or myc-sufu (lane 5) alone but is present when cells are cotransfected with both constructs (lane 6).

FIGS. 4A–F. In 4A the localization of SUFUH primarily to the cytoplasmic compartment but also in the nucleus is shown after transfection of an EGFP tagged expression construct to human 293 cells. Localization to both the cytoplasmic and nuclear compartments is confirmed by subcellular fractionation followed by Western blotting as shown in 4B by transfection of a myc-epitope tagged construct to 293 cells.

The cytoplasmic localization of EGFP tagged wild-type GLI-1 is demonstrated in 4C. In 4D nuclear localization of a truncated GLI-1 protein is shown and in 4E the primarily cytoplasmic localization of this truncated GLI-1 when co-transfected with an expression vector for SUFUH is demonstrated. FIG. 4F shows in an EMSA assay that SUFUH alters the mobility of the complex containing the truncated GLI-1 bound to a concensus GLI-DNA-response element indicating the ability of SUFUH to interact also with DNA-bound GLI-1.

Figure 5:
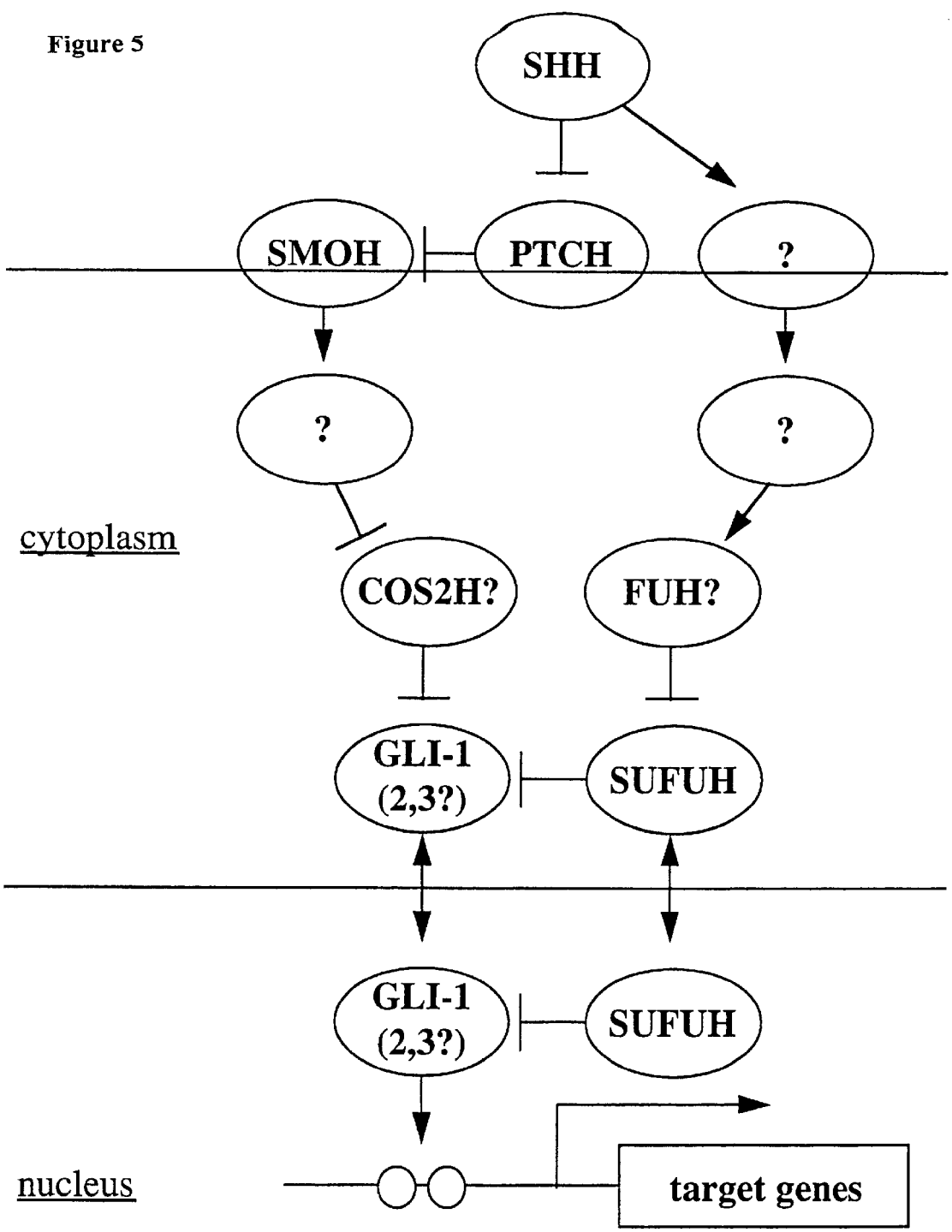
FIG. 5 is a model for the role of human suppressor of fused in the SHH-PTCH-GL1 signal transduction pathways.

FIG. 5. Model for the role of SUFUH in the SHH-PTCH-GLI signal transduction pathways. Based on ouI data as well as some additional evidence as discussed in the text we propose that Fu and Su(fu) represent an additional arm in the pathway that exerts independent control on GLI (Ci) activity.

Definitions

The term "antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively. Antibodies exist e.g., as intact immunoglobulins or as a number of well characterized fragments produced by digestion with various peptidases. Thus, for example, pepsin digests an antibody below the disulfide linkages in the hinge region to produce $F(ab)'_2$, a dimer of Fab which itself is a light chain joined to $V_H$—$C_H$ 1 by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially an Fab with pair of the hinge region (see, *Fundamental Immunology,* Third Edition, W. E. Paul, ed., Raven Press, N.Y. 1993). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "immunoassay" is an assay that utilizes an antibody to specifically bind an analyte. The immunoassay is characterized by the use of specific binding properties of a particular antibody to isolate, target, and/or quantify the analyte. The terms "isolated" "purified" or "biologically pure" refer to material which is substantially or essentially free from components which normally accompany it as found in its native state.

The term "nucleic acid" refers to a deoxyribonucleotide or ribonucleotide polymer in either single- or double-stranded form, and unless otherwise limited, encompasses known analogs of natural nucleotides that can function in a similar manner as naturally occurring nucleotides.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally ocurring amino acid polymers.

A "label" is a composition detectable by spectroscopic, photochemical, biochemical, immunochemical, or chemical means. For example, useful labels include $^{32}P$, fluorescent dyes, electron-dense reagents, enzymes (e.g., as commonly used in a ELISA), biotin, dioxigenin, or haptens and proteins for which antisera or monoclonal antibodies are available (e.g., the peptide of SEQ ID NO 1 can be made detectable, e.g., by incorporating a radio-label into the peptide, and used to detect antibodies specifically reactive with the peptide).

As used herein a "nucleic acid probe" is defined as a nucleic acid capable of binding to a target nucleic acid of complementary sequence through one or more types of chemical bonds, usually through complementary sequence pairing, usually through hydrogen bond formation. As used herein, a probe may include natural (i.e. A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather that phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphore, chromogenis, or indirectly labeled such as with biotin to which a streptavidin complex may later bind. By assaying for the presence or absence of the probe, one can detect the presence or absence of the select sequence or subsequence.

A "labeled nucleic acid probe" is a nucleic acid probe that is bound, either covalently, through a linker, or through ionic, van der Waals of hydrogen bonds to a label such that the presence of the probe may be detected by detecting the presence of the label bound to the probe.

The term "target nucleic acid" refers to a nucleic acid (often derived from a biological sample), to which a nucleic acid probe is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding probe directed to the target. The term target nucleic acid may refer to the specific subsequence of a larger nucleic acid to which the probe is directed or to the ovarall sequence (e.g., gene or mRNA) whose expression level it is desired to detect. The difference in usage will be apparent from context.

"Subsequence" refers to a sequence of nucleic acids or amino acids that comprise a part of a longer sequence of nucleic acids or amino acids (e.g., polypeptide), respectively.

The term "recombinant" when used with reference to a cell, or nucleic acid, or vector, indicates that the cell, or nucleic acid, or vector, has been modified by the introduction of a heterologous nucleic acid or the alteration of a native nucleic acid, or that the cell is derived from a cell so modified. Thus, for example, recombinant cells express genes that are not found within the native (non-recombinant) form of the cell or express native genes that are otherwise abnormally expressed, under expressed or not expressed at all. The term "identical" in the context of two nucleic acids or polypeptide sequences refers to the residues in the two sequences which are the same when aligned for maximum correspondence. Optimal alignment of sequences for comparison can be conducted, e.g., by the local homology algorithm of Smith and Waterman (1981) *Adv. Appl. Math.* 2: 482, by the homology alignment algorithm of Needleman and Wunsch (1970) *J. Mol. Biol.* 48:443, by the search for similarity method of Pearson and Lipman (1988) *Proc. Natl. Acad. Sci. USA* 85: 2444, by computerized implementations of these algorithms (GAP, BESTFIT, FASTA, and TFASTA in the Wisconsin Genetics Software Package, Genetics Computer Group, 575 Science Dr., Madison, Wis.) or by inspection.

An additional algorithm that is suitable for determining sequence similarity is the BLAST algorithm, which is described in Altschul et al. (1990), *J. Mol. Biol.* 215: 403–410. Software for performing BLAST analyses is publicly available through the National Center for Biotechnology Information (http//www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold (Altschul et al, supra.) These initial neighborhood word hits act as seeds for initiating searches to find longer HSPs containing them. The word hits are extended in both directions along each sequence for as fas as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or, the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915–10919) alignments (B) of 50, expectation (E) of 10, M=5, N=4, and a comparison of both strands. The BLAST algorithm performs a statistical analysis of the similarity between two sequences; see e.g., Karlin and Altschul (1993) *Proc. Nat'l Acad. Sci. USA* 90: 5873–5787. One measure of similarity provided by the BLAST algorithm is the smallest sum probability (P(N)), which provides an indication of the probability by which a match between two nucleotide or amino acid sequences would occur by chance. For example, a nucleic acid is considered similar to a suppressor of fused gene or cDNA if the smallest sum probability in a comparison of the test nucleic acid to a suppressor of fused nucleic acid is less than about 1, preferably less than about 0.1, more preferably less than about 0.01, and most preferably less than about 0.001.

The term "substantial identity" or "substantial similarity" in the context of a polypeptide indicates that a polypeptides comprises a sequence with at least 70% sequence identity to a reference sequence, or preferably 80%, or mole preferably 85% sequence identity to the reference sequence, or most preferably 90% identity over a comparison window of about 10–20 amino acid residues. An indication that two polypeptide sequences are substantially identical is that one peptide is immunologically reactive with antibodies raised against the second peptide. Thus, a polypeptide is substantially identical to a second polypeptide, for example, where the two peptides differ only by a conservative substitution.

An indication that two nucleic acid sequences are substantially identical is that the polypeptide which the first nucleic acid encodes is immunologically cross reactive with the polypeptide encoded by the second nucleic acid.

Another indication that two nucleic acid sequences are substantially identical is that the two molecules hybridize to each other under stringent conditions.

"Bind(s) substantially" refers to complementary hybridization between a probe nucleic acid and a target nucleic acid and embraces minor mismatches that can be accomodated by reducing the stringency of the hybridization media to achieve the desired detection of the target polynucleotide sequence.

The phrase "hybridizing specifically to", refers to the binding, duplexing, or hybridizing of a molecule only to a particular nucleotide sequence under stringent conditions when that sequence is present in a complex mixture (e.g., total cellular) DNA or RNA. The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point Tm for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupies at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

The phrases "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual,* Cold Spring Harbour Publications, New York, for a description of immunoassay formats and conditions that can be used to determine specific immunoreactivity.

A "conservative substitution", when describing a protein, refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), glutamine (Q),
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) *Protein,* W.H. Freeman and Company. In addition, individual substitutions, deletions or additions which alter, add or delete a single amino acid or a small percentage of amino acids in an encoded sequence are also "conservatively modified variations".

A "gene product", as used herein, refers to a nucleic acid whose presence, absence, quantity, or nucleic acid sequence is indicative of a presence, absence, quantity, or nucleic acid composition of the gene. Gene products thus include, but are not limited to, a mRNA transcript, a cDNA reverse transcribed from a mRNA, and RNA transcribed from that cDNA, a DNA amplified from the cDNA, an RNA transcribed from the amplified DNA or subsequences of any of these nucleic acids. Polypeptides expressed by the gene or subsequences thereof are also gene products. The particular type of gene product will be evident from the context of the usage of the term.

EXPERIMENTAL

General Methods

I

B) Isolation of cDNA and/or Probes

The nucleic acids of the present invention are cloned, or amplified by in vitro methods, such as the polymerase chain reaction (PCR), the ligase chain reaction (LCR), the transcription-based amplification system (TAS), the self-sustained sequence replication system (SSR). A wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Technique, Methods in Enzymology* 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring harbor Press, NY, (Sambrook et al.); *Current Protocols in Molecular Biology,* F. M. Ausubel et al., Current Protocols, a joint venture between Greene Publishing Associates, Inc. And John Wiley & Sons, Inc., (1994 Supplement) (Ausubel); Cashion et al., U.S. Pat. No. 5,017,478; and Carr, European Patent No 0.246,864. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al. Eds) Academic Press Inc. San Diego. Calif. ( 1990) (Innis); Arnheim & Levinson (Oct. 1, 1990)*C&EN* 36–47; *The Journal Of NIH Research* (1991) 3: 81–94 (Kwoh et al. (1989) *Proc. Natl. Acad. Sci. USA.* 86: 1173; Guatelli et al. (1990) *Proc. Natl. Acad. Sci. USA* 87, 1874; Lomell et al. (1989) *J. Clin. Chem.,* 35: 1826; Landegren et al., (1988) *Science,* 241: 1077–1080; Van Brunt (1990) *Biotechnology,* 8: 291–294; Wu and Wallace, (1989) *Gene,* 4: 560; and Barringer et al. (1990) *Gene,* 89: 117.

In one preferred embodiment, the human suppressor of fused cDNA can be isolated by routine cloning methods. The cDNA sequence provided in SEQ ID NO 1 can be used to provide probes that specifically hybridize to the suppressor of fused gene, in a genomic DNA sample, or to the suppressor of fused mRNA, in a total RNA sample (e.g., in a Southern blot). Once the target suppressor of fused nucleic acid is identified (e.g., in a Northern blot), it can be isolated according to standard methods known to those of skill in the art (see, e.g., Sambrook et al. (1989) *Molecular Cloning: A Laboratory Manual, 2nd Ed. Vols.* 1–3, Cold Spring Harbor Laboratory; Berger and Kimmel (1987) *Methods in enzymology, Vol.* 152: *Guide to Molecular Cloning Techniques,* San Diego: Academic press, Inc.; or Ausubel et al. (1987) *Current Protocols in Molecular Biology,* Greene Publishing and Wiley-Interscience, New York).

In another preferred embodiment, the human suppressor of fused cDNA can be isolated by amplification methods such as polymerase chain reaction (PCR).

II

C) Labeling of Nucleic Acid Probes

Where the suppressor of fused cDNA or its subsequences are to be used as nucleic acid probes, it is often desirable to label the sequences with detectable labels. The labels may be incorporated by any of a number of means well known to those of skill in the art. However, in a preferred embodiment, the label is simultaneously incorporated during the amplification step in the preparation of the sample nucleic acids. Thus, for example, polymerase chain reaction (PCR) with labeled primers or labeled nucleotides will provide a labeled amplification product. In another preferred embodiment, transcription amplification using a labeled nucleotide (e.g. fluorescein-labeled UTP and/or CTP) incorporates a label into the transcribed nucleic acids.

Alternatively, a label may be added directly to an original nucleic acid sample (e.g., mRNA, polyA mRNA, cDNA, etc.) or to the amplification product after the amplification is completed. Means of attaching labels to nucleic acids are well known to those of skill in the art and include, for example nick translation or end labeling (e.g. with a labeled RNA) by kinasing of the nucleic acid and subsequent attachment (ligation) of a nucleic acid linker joining the sample nucleid acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as collodial gold or colored glass or plastic (e.g., polystyrene, polypropylene, latex, etc.) beads. Patents teaching the use of such labels include U.S. Pat. Nos. 3,871,837; 3,850,752; 3,939,350; 3,996,345; 4,277,437; 4,275,149; and 4,366,241.

Means of detecting such labels are well known to those of skill in the air. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

III

Antibodies to the Suppressor of Fused Polypeptide(s)

Antibodies are raised to the polypeptides of the present invention, including individual, ellelic, strain, or species variants, and fragments thereof, both in their naturally occurring (full-length) forms and in recombinant forms. Additionally, antibodies are raised to these polypeptides in either their native configurations or in non-native configurations. Anti-idiotypic antibodies can also be generated. Many methods of making antibodies are known to persons of skill. The following discussion is presented as a general overview of the techniques available; however, one of skill will recognize that many variations upon the following methods are known.

A) Antibody Production

A number of immunogens are used to produce antibodies specifically reactive with polypeptides according to the invention. Recombinant or synthetic polypeptides of 8–15, preferably 10, amino acids in length, or greater, selected from amino acid sub-sequences of SEQ ID NO 2 are the preferred polypeptide immunogen (antigen) for the production of monoclonal or polyclonal antibodies. In one class of preferred embodiments, an immunogenic peptide conjugate is also included as an immunogen. Naturally occurring polypeptides are also used, either in pure or impure form.

Recombinant polypeptides are expressed in eukaryotic or prokaryotic cells (as described below) and purified using standard techniques. The polypeptide, or a synthetic version thereof, is then injected into an animal capable of producing antibodies. Either monoclonal or polyclonal antibodies can be generated for subsequent use in immunoassays to measure the presence and quantity of the polypeptide.

Methods of producing polyclonal antibodies are known to those of skill in the art. In brief, an immunogen (antigen), preferably a purified polypeptide, a polypeptide coupled to an appropriate carrier (e.g., GST, keyhole limper hemanocyanin, etc.), or a polypeptide incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the polypeptide of interest. When appropriately high titers of antibody to the immunogen are obtained, blood is collected from the animal and antisera are prepared. Further fractionation of the antisera to enrich for antibodies reactive to the polypeptide is performed where desired (see, e.g., Coligan (1991) *Current Protocol in Immunology* Wiley/Greene, NY; and Harlow and Lane (1989) *Antibodies: A Laboratory Manual* Cold Spring Harbor Press, NY).

Antibodies, including binding fragments and single chain recombinant versions thereof, against predetermined fragments of the present polypeptides are raised by immunizing animals, e.g., with conjugates of the fragments with carrier proteins as described above. Typically, the immunogen of interest is a peptide of at least about 5 amino acids, more typically the peptide is 10 amino acids in length, preferably, the fragment is 15 amino acids in length and more preferably the fragment is 20 amino acids in length or greater. The peptides are typically coupled to a carrier protein (e.g., as a fusion protein), or are recombinantly expressed in an immunization vector. Antigenic determinants on peptides to which antibodies bind are typically 3 to 10 amino acids in length.

Monoclonal antibodies are prepared from cells secreting the desired antibody. These antibodies are screened for binding to normal or modified polypeptides, or screened for agonistic or antagonistic activity, e.g., activity mediated through a suppressor of fused protein. Specific monoclonal and polyclonal antibodies will usually bind with a $K_D$ of at least about 0.1 mM, more usually at least about 50 $\mu$M, and most preferably at least about 1 $\mu$M or better.

In some instances, it is desirable to prepare monoclonal antibodies from various mammalian hosts, such as mice, rodents, primates, humans, etc. Description of techniques for preparing such monoclonal antibodies are found in, e.g. Stites et al. (eds) *Basic and Clinical Immunology* (4th ed.) Lange Medical Publications, Los Altos, Calif., and references cited therin; Harlow and Lane, supra; Goding (1986) *Monoclonal Antiboides: Principles and Practice* (2d ed.) Academic Press, New York, N.Y.; and Kohler and Milstein (1975) *Nature* 256: 495–497. Summarized briefly, this method proceeds by injecting an animal with an immunogen. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells in enhanced by various techniques, including injection into the peritoneal cavity of a vertebrate (preferably mammalian) host. The polypeptides and antibodies of the present invention are used with or without modification, and include chimeric antibodies such as humanized murine antibodies.

Other suitable techniques involve selection of libraries of recombinant antibodies in phage or similar vectors (see, e.g., Huse et al. (1989) *Science* 246: 1275–1281; and Ward, et al. (1989) *Nature* 341: 544–546; and Vaughan et al. (1996) *Nature Biotechnology*, 14: 309–314).

Frequently, the polypeptides and antibodies will be labeled by joining, either covalently or non-covalently, a substance which provides for a detectable signal. A wide variety of labels, and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350, 3,996,345; 4,277,437; 4,275,149; and 4,366,241. Also recombinant immunoglobulins may be produced. See, Cabalitty, U.S. Pat. No. 4,816, 567; and Queen et al. (1989) *Proc. Nat'l Acad. Sci. USA* 86: 10029–10033.

The antibodies of this invention are also used for affinity chromatography in isolating suppressor fused polypeptides. Columns are prepared, e.g., with the antibodies linked to a solid support, e.g., particles such as agarose, Sephadex, or the like, where a cell lysate is passed through the column, washed, and treated with increasing concentrations of a mild denaturant, whereby purified suppressor of fused polypeptides are released.

The antibodies can be used to screen expression libraries for particular expression products such as normal or abnormal human suppressor of fused protein. Usually the antibodies in such a procedure are labeled with a moiety allowing easy detection of presence of antigen by antibody binding.

Antibodies raised against suppressor of fused polypeptides can also be used to raise antiidiotypic antibodies. These are useful for detecting or diagnosing various pathological conditions related to the presence of the respective antigens.

B) Human or Humanized (Chimeric) Antibody Production

The antibodies of this invention can also be administered to an organism (e.g., a human patient) for therapeutic purposes. Antibodies administered to an organism other than the species in which they are raised are often immunogenic. Thus, for example, murine antibodies administered to a human often induce an immunologic response against the antibody (e.g., the human anti-mouse antibody (HAMA) response) on multiple administrations. The immunogenic properties of the antibody are reduced by altering portions, or all, of the antibody into characteristically human sequences thereby producing chimeric or human antibodies, respectively.

i) Humanized (Chimeric) Antibodies

Humanized (chimeric) antibodies are immunoglobulin molecules comprising a human and non-human portion. More specifically, the antigen combining region (or variable region) of a humanized chimeric antibody is derived from a non-human source (e.g., murine) and the constant region of the chimeric antibody (which confers biological effector function to the immunoglobulin) is derived from a human source. The humanized chimeric antibody should have the antigen binding specificity of the non-human antibody molecule and the effector function conferred by the human antibody molecule. A large numer of methods of generating chimeric antibodies are well known to those of skill in the art (see, e.g., U.S. Pat. Nos.: 5,502,167, 5,500,362, 4,491,088, 5,482,856, 5,472,693, 5,354,847, 5,292,867, 5,231,026, 5,204,244, 5,202,238, 5,169,939, 5,081,235, 5,075,431, and 4,975,369).

In general, the procedures used to produce these chimeric antibodies consist of the following steps (the order of some steps may be interchanged): (a) identifying and cloning the correct gene segment encoding the antigen binding portion of the antibody molecule; this gene segment (known as the DVJ, variable, diversity and joining regions for heavy chains or VJ, variable, joining regions, for light chains (or simply as the V or Variable region) may be in either the cDNA or genomic form; (b) cloning the gene segments encoding the constant region or desired part thereof; (c) ligating the variable region to the constant region so that the complete chimeric antibody is encoded in a transcribable and translatable form; (d) ligating this construct into a vector containing a selectable marker and gene control regions such as promoters, enhancers and poly(A) addition signals; (e) amplifying this construct in a host cell (e.g., bacteria; (f) introducing the DNA into eukaryotic cells (transfections) most often mammalian lymphocytes; and culturing the host cell under conditions suitable for expression of the chimeric antibody. Antibodies of several distinct antigen binding specificities have been manipulated by these protocols to produce chimeric proteins (e.g., anti-TNP: Boulianne et al. (1984) Nature, 312: 643; and anti-tumor antigens: Sahagan et al. (1986) J. Immunol., 137: 1066). Likewise several different effector functions have been achieved by linking new sequences to those encoding the antigen binding region. Some of these include enzymes (Neuberger et al. (1984) Nature 312:604), immunoglobulin constant regions from another species and constant regions of another immunoglobulin chain (Sharon et al. (1984) Nature 309: 364; Tan et al., (1985) J. Immunol. 135: 3565–3567).

In one preferred embodiment, a recombinant DNA vector is used to transfect a cell line that produces an anti-suppressor of fused antibody. The novel recombinant DNA vector contains a "replacement gene" to replace all or a portion of the gene encoding the immunoglobulin constant region in the cell line (e.g., a replacement gene may encode all or a portion of a constant region of a human immunoglobulin, a specific immunoglobulin class, or an enzyme, a toxin, a biologically active peptide, a growth factor, inhibitor, or a linker peptide to facilitate conjugation to a drug, toxin, or other molecule, etc.), and a "target sequence" which allows for targeted homologous recombination with immunoglobulin sequences within the antibody producing cell.

In another embodiment, a recombinant DNA vector is used to transfect a cell line that produces an antibody having a desired effector function, (e.g., a constant region of a human immunoglobulin) in which case, the replacement gene contained in the recombinant vector may encode all or a portion of a region of an anti-suppressor of fused antibody and the target sequence contained in the recombinant vector allows for homologous recombination and targeted gene modification within the antibody producing cell. In either embodiment, when only a portion of the variable or constant region is replaced, the resulting chimeric antibody may define the same antigen and/or have the same effector function yet be altered or improved so that the chimeric antibody may demonstrate a greater antigen specificity, greater affinity binding constant, increased effector function, or increased secretion and production by the transfected antibody producing cell line, etc.

Regardless of the embodiment practiced, the processes of selection for integrated DNA (via a selectable marker), screening for chimeric antibody production, and cell cloning, can be used to obtain a clone of cells producing the chimeric antibody.

Thus, a piece of DNA which encodes a modification for a monoclonal antibody can be targeted directly to the site of the expressed immunoglobulin gene within a B-cell or hybridoma cell line. DNA constructs for any particular modification may be used to alter the protein product of any monoclonal cell line or hybridoma. Such a procedure circumvents the costly and time consuming task of cloning both heavy and light chain variable region genes from each B-cell close expressing a useful antigen specificity. In addition to circumventing the process of cloning variable region genes, the level of expression of chimeric antibody should be higher when the gene is at its natural chromosomal location rather than at a random position. Detailed methods for preparation of chimeric (humanized) antibodies can be found in U.S. Pat. No. 5,482,856.

ii) Human Antibodies

In another embodiment, this invention provides for fully human anti-suppressor of fused antibodies. Human antibodies consist entirely of characteristically human polypeptide sequences. The human antibodies of this invention can be produced in using a wide variety of methods (see, e.g., Larrick et al., U.S. Pat. No 5,001,065, for review).

In one preferred embodiment, the human antibodies of the present invention are usually produced initially in trioma cells. Genes encoding the antibodies are then cloned and expressed in other cells, particularly, nonhuman mammalian cells.

The general approach for producing human antibodies by trioma technology has been described by Ostberg et al. (1983) Hybridoma 2: 361–367, Ostberg, U.S. Pat. No. 4,634,664, and Engelman et al. U.S. Pat. No. 4,634,666. The antibody-producing cell lines obtained by this method are called triomas because they are descended from three cells; two human and one mouse. Triomas have been found to produce antibody more stably than ordinary hybridomas made from human cells.

Preparation of trioma cells requires an initial fusion of a mouse myeloma cell line with unimmunized human peripheral B lymphocytes. This fusion generates a xenogenic hybrid cell containing both human and mouse chromosomes (see, Engelman, supra.). Xenogenic cells that have lost the capacity to secrete antibodies are selected. Preferably, a xenogenic cell is selected that is resistant to 8-azaguanine. Cells possessing resistance to 8-azaguanine are unable to propagate on hypoxanthine-aminopterin-thymidine (HAT) or azaserine-hypoxanthine (AH) media.

The capacity to secrete antibodies is conferred by a further fusion between the xenogenic cell and B-lymphocytes immunized against a polypeptide according to the invention or an epitope thereof. The B-lymphocytes are obtained from the spleen, blood or lymph nodes of human donors. If antibodies against a specific antigen or epitope are desired, it is preferable to use that antigen or epitope thereof as the immunogen rather than suppressor of fused polypeptide. Alternatively, B-lymphocytes are obtained from an unimmunized individual and stimulated with the present polypeptide, or an epitope thereof, in vitro. In a further variation, B-lymphocytes are obtained from an infected, or otherwise immunized individual, and then hyperimmunized by exposure to a suppressor of fused polypeptide for about seven to fourteen days, in vitro.

The immunized B-lymphocytes prepared by one of the above procedures are fused with a xenogenic hybrid cell by well known methods. For example, the cells are treated with 40–50% polyethylene glycol of MW 1000–4000, at about 37° C. for about 5–10 min. Cells are separated from the fusion mixture and propagated in media selective for the desired hybrids. When the xenogenic hybrid cell is resistant to 8-azaguanine, immortalized trioma cells are conveniently selected by successive passage of cells on HAT or AH medium. Other selective procedures are, of course, possible depending on the nature of the cells used in fusion. Clones secreting antibodies having the required binding specificity are identified by assaying the trioma culture medium for the ability to bind to the present polypeptide or an epitope thereof. Triomas producing human antibodies having the desired specificity are subcloned by the limiting dilution technique and grown in vitro in culture medium or are injected into selected host animals and grown in vitro.

The trioma cell lines obtained are then tested for the ability to bind a polypeptide or an epitope thereof. Antibodies are separated from the resulting culture medium or body fluids by conventional antibody-fractionation procedures, such as ammonium sulfate precipitation, DEAE cellulose chromatography and affinity chromatography.

Although triomas are genetically stable they do not produce antibodies at very high levels. Expression levels can be increased by cloning antibodies genes from the trioma into one or more expression vectors, and transforming the vector into a cell line such as the cell lines typically used for expression of recombinant or humanized immunoglobulins. As well as increasing yield of antibody, this strategy offers the additional advantage that immunoglobulins are obtained from a cell line that does not have a human component, and does not therefore need to be subjected to the especially extensive viral screening required for human cell lines.

The genes encoding the heavy and light chains of immunoglobulins secreted by trioma cell lines are cloned according to methods, including the polymerase chain reaction, known in the art (see, e.g., Sambrook et al., *Molecular Cloning: A Laboratory Manual,* 2nd ed., Cold Spring Harbor, N.Y., 1989; Berger & Kimmel, *Methods in Enzymology, Vol.* 152: *Guide to Molecular Cloning Techniques,* Academic Press, Inc., San Diego, Calif., 1987; Co et al. (1992) *J. Immunol.,* 148: 1149). For example, genes encoding heavy and light chains are cloned from a trioma's genomic DNA or cDNA produced by reverse transcription of the trioma's RNA. Cloning is accomplished by conventional techniques including the use of PCR primers that hybridize to the sequences flanking or overlapping the genes, or segments of genes, to be cloned.

Typically, recombinant constructs comprise DNA segments encoding a complete human immunoglobulin heavy chain and/or a complete human immunoglobulin light chain of an immunoglobulin expressed by a trioma cell line. Alternatively, DNA segments encoding only a portion of the primary antibody genes are produced, which portions possess binding and/or effector activities. Other recombinant constructs contain segments of trioma cell line immunoglobulin genes fused to segments of other immunoglobulin genes, particularly segments of other human constant region sequences (heavy and/or light chain). Human constant region sequences can be selected from various reference sources, including but not limited to those listed in Kabat et al. (1987) *Sequences of Proteins of Immunological Interest,* U.S. Department of Health and Human Services.

In addition to the DNA segments encoding anti-suppressor of fused immunoglobulins or fragments thereof, other substantially homologous modified immunoglobulins can be readily designed and manufactured utilizing various recombinant DNA techniques known to those skilled in the art such as site-directed mutagenesis (see Gillman & Smith (1979) *Gene,* 8: 81–97; Roberts et al. (1987) *Nature* 328: 731–734). Such modified segments will usually retain antigen binding capacity and/or effector function. Moreover, the modified segments are usually not so far changed from the original trioma genomic sequences to prevent hybridization to these sequences under stringent conditions. Because, like many genes, immunoglobulin genes contain separate functional regions, each having one or more distinct biological activites, the genes may be fused to functional regions from other genes to produce fusion proteins (e.g., immunotoxins) having novel properties or novel combinations of properties.

The recombinant polynucleotide constructs will typically include an expression control sequence operably linked to the coding, sequences, including naturally associated or heterologous promoter regions. Preferably, the expression control sequences will be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the human anti-suppressor of fused immunoglobulins.

These expression vectors are typically replicable in the host organisms either as episomes or as an integral part of the host chromosomal DNA. Commonly, expression vectors will contain selection markers, e.g. impicillin-resistance or hygromycin-resistance, to permit detection of those cells transformed with the desired DNA sequences.

In general, prokaryotes can be used for cloning the DNA sequences encoding a human anti-suppressor of fused immunoglobulin chain. *E. coli* is one prokaryotic host particularly useful for cloning the DNA sequences of the present invention. Microbes, such as yeast are also useful for expression. Saccharomyces is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase 2, isocytochrome C, and enzymes responsible for maltose and galactose utilization.

Mammalian cells are a particularly preferred host for expressing nucleotide segments encoding immunoglobulins or fragments thereof (see, e.g. Winnacker, *From Genes to Clones,* VCH Publishers, N.Y., 1987). A number of suitable host cell lines capable of secreting intact heterologous proteins have been developed in the art, and include CHO cell lines, various COS cell lines, HeLa cells, L cells and myeloma cell lines. Preferably, the cells are nonhuman. Expression vectors for these cells can include expression control sequences, such as an origin of replication, a promoter, an enhancer (Queen et al. (1986) *Immunol. Rev.*

89:49), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine pappillomavirus, and the like (see, e.g., Co et al. (1992) *J. Immunol.* 1458: 1149).

The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics or viral-based transfection may be used for other cellular hosts. Other methods used to transform mammalian cells include the use of polybrene, protoplast fusion, liposomes, electroporation, and microinjection (see, generally, Sambrook et al., supra).

Once expressed, human anti-suppressor of fused immunoglobulins of the invention can be purified according to standard procedures of the art, including HPLC purification, fraction column chromatography, gel electrophoresis and the like (see, generally, Scopes, *Protein Purification,* Springer-Verlag, NY, 1982). Detailed protocols for the production of human antibodies can be found in U.S. Pat. No. 5,506,132.

Other approaches in vitro immunization of human blood. In this approach, human blood lymphocytes capable of producing human antibodies are produced. Human peripheral blood is collected from the patient and is treated to recover mononuclear cells. The suppressor T-cells then are removed and remaining cells are suspended in a tissue culture medium to which is added the antigen and autologous serum and, preferably, a nonspecific lymphocyte activator. The cells then are incubated for a period of time so that they produce the specific antibody desired. The cells then can be fused to human myeloma cells to immortalize the cell line, thereby to permit continuous production of antibody (see U.S. Pat. No. 4,716,111).

In another approach, mouse-human hybridomas which produces human anti-suppressor of fused are prepared (see, e.g. U.S. Pat. No. 5,506,132). Other approaches include immunization of murines transformed to express human immunoglobulin genes, and phage display screening (Vaughan et al. Supra).

IV

Expression of Suppressor of Fused Polypeptides

A) De novo Chemical Synthesis

The present proteins or subsequences thereof may be synthesized using standard chemical peptide synthesis techniques. Where the desired subsequences are relatively short (e.g., when a particular antigenic determinant is desired), the molecule may be synthesized as a single contiguous polypeptide. Where larger molecules are desired, subsequences can be synthesized separately (in one or more units) and then fused by condensation of the amino terminus of one molecule with the carboxyl terminus of the other molecule thereby forming a peptide bond.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, *Solid-Phase Peptide Synthesis;* pp. 3–284 in *The Peptides: Analysis, Synthesis, Biology. Vol.* 2: *Special Methods in peptide Synthesis, Part A.,* Merrifiled, et al. *J. Am. Chem. Soc.,* 85: 2149–2156 (1963), and Stewart et al., *Solid Phase Peptide Synthesis,* 2nd ed. Pierce Chem. Co., Rockford, Ill. (1984).

B. Recombinant Expression

In a preferred embodiment, the present proteins or subsequences thereof, are synthesized using recombinant DNA methodology. Generally this involves creating a DNA sequence that encodes the fusion protein, placing the DNA in an expression casette under the control of a particular promoter, expressing the protein in a host, isolating the expressed protein and, if required, renaturing the protein.

DNA encoding the present proteins or subsequences of this invention may be prepared by any suitable method as described above, including, for example, cloning and restriction of appropriate sequences or direct chemical synthesis by methods such as the phosphotriester method of Narang et al. *Meth. Enzymol.* 68: 90–99 (1979); the phosphodiester method of Brown et al., *Meth Enzymol.* 68: 109–151 (1979); the diethylphosphoramidite method of Beaucage et al., *Tetra. Lett.,* 22: 1859–1862 (1981); and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Alternatively, subsequences may be cloned and the appropriate subsequences cleaved using appropriate restriction enzymes. The fragments may then be ligated to produce the desired DNA sequence.

In one embodiment, proteins of this invention may be cloned using DNA amplification methods such as polymerase chain reaction (PCR). Thus, for example, the nucleic acid sequence or subsequence is PCR amplified, using a sense primer containing one restriction site (e.g., NdeI) and an antisense primer containing another restriction site (e.g., HindIII). This will produce a nucleic acid encoding the desired sequence or subsequence and having terminal restriction sites. This nucleic acid can then be easily ligated into a vector containing a nucleic acid encoding the second molecule and having the appropriate corresponding restriction sites. Suitable PCR primers can be determined by one of skill in the art using the Sequence information provided in SEQ ID No: 1. Appropriate restriction sites can also be added to the nucleic acid encoding the protein or protein subsequence by site-directed mutagenesis. The plasmid containing the sequence or subsequence is cleaved with the appropriate restriction endonuclease and then ligated into the vector encoding the second molecule according to standard methods.

The nucleic acid sequences encoding suppressor of fused proteins or protein subsequences may be expressed in a variety of host cells, including *E. coli,* other bacterial hosts, yeast, and various higher eukaryotic cells such as the COS, CHO and HeLa cells lines and myeloma cell lines. As the present proteins are typically found in eukaryotes, a eukaryote host is preferred. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably and enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant proteins according to the invention can be purified according to standard procedures of the art, including ammonium sulfate precipitation, affinity columns, column chromatography, gel electrophoresis and the like (see, generally, R. Scopes, *Protein Purification,* springer-Verlag, N.Y. (1982), Deutscher, *Methods in Enzymology Vol.* 183: *Guide to Protein Purification.,* Academic Press, Inc. N.Y. (1990)). Substantially pure compositions of at least about 90 to 95% homogenity are preferred, and 98 to 99% or more homogenity are most preferred. Once purified, partially or to homogeneity as desired, the polypeptides may then be used (e.g., immunogens for antibody production).

One of skill in the all would recognize that after chemical synthesis, biological expression, or purification, the present protein(s) may possess a conformation substantially different than the native conformations of the constituent polypeptides. In this case, it may be necessary to denature and reduce the polypeptide and then to cause the polypeptide to re-fold into the preferred conformation. Methods or reducing and denaturing proteins and inducing re-folding are well known to those of skill in the all (See, Debinski et al. (1993) *J. Biol. Chem.,* 268: 14065–14070; Kreitman and pastan (1993) *Bioconjug. Chem.,* 4: 581–585; and Buchner, et al., (1992) *Anal. Biochem.,* 205: 263–270). Debinski et al., for example, describe the denaturation and reduction of inclusion body proteins in guanidine-DTE. The protein is then refolded in a redox buffer containing oxidized glutathione and L-arginine.

One of skill would recognize that modifications can be made to the suppressor of fused proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

V

Detection of Suppressor of Fused

As indicated above, abnormal (e.g., altered or deficient) expression of the human suppressor of fused gene is beleived to be a causal factor in the development of several different conditions, such as cancers. Thus, it is desirable to determine the presence or absence, or quantify, the expression of suppressor of fused polypeptides of the nucleic acids encoding the suppressor of fused polypeptides. This may be accomplished by assaying the gene product; suppressor of fused polypeptides themselves, or alternatively, by assaying the nucleic acids (DNA or mRNA) that encode the suppressor of fused polypeptides. In particular, it is desirable to determine whether suppressor of fused expression is presents absent, or abnormal (e.g., because of an abnormal gene product or because of abnormal expression levels as, for example, with a hemizygous gene). Particularly, where it is desired to determine a heritable propensity for abnormal suppressor of fused gene expression, it is preferred to assay the host DNA for abnormal suppressor of fused genes or gene transcripts (mRNAs).

A) Sample Collection and Processing

The suppressor of fused gene or gene product (i.e., mRNA or polypeptide) is preferably detected and/or quantified in a biological sample. As used herein, a biological sample is a sample of biological tissue or fluid that, in a healthy and/or pathological state, contains a suppressor of fused nucleic acid or polypeptide. Such samples include, but are not limited to, sputum, amniotic fluid, blood, blood cells (e.g., white cells), tissue or fine needle biopsy samples, urine, peritoneal fluid, and pleural fluid, or cells therefrom. Biological samples may also include sections of tissues such as frozen sections taken for histological purposes. Although the sample is typically taken from a human patient, the assays can be used to detect suppressor of fused genes or gene products in samples from any mammal, such as dogs, cats, sheep, cattle, and pigs.

The sample may be pretreated as necessary by dilution in a appropriate buffer solution or concentrated, if desired. Any of a number of standard aqueous buffer solutions, employing one of a variety of buffers, such as phosphate, Tris, or the like, at physiological pH can be used.

B) Nucleic Acid Assays

In one bodiment, this invention provides for methods of detecting and/or quantifying human suppressor of fused expression by assaying the underlying suppressor of fused gene (or a fragment thereof) or by assaying the suppressor of fused gene transcript (mRNA). The assay can be for the presence or absence of the normal gene or gene product, for the presence or absence of an abnormal gene or gene product, or quantification of the transcription levels of normal or abnormal suppressor of fused gene product.

i) Nucleic Acid Sample

In a preferred embodiment, nucleic acid assays are performed with a sample of nucleic acid isolated from the organism to be tested. In the simplest embodiment, such a nucleic acid sample is the total mRNA isolated from a biological sample. The nucleic acid (e.g., either genomic DNA or mRNA) may be isolated from the sample according to any of a number of methods well known to those of skill in the art. One of skill will appreciate that where alterations in the copy number of the suppression of fused gene are to be detected genomic DNA is preferably isolated. Conversely, where expression levels of a gene or genes are to be detected, preferably RNA (mRNA) is isolated.

Methods of isolating total DNA or mRNA are well known to those of skill in the art. For example, methods of isolation and purification of nucleic acids are described in detail in Chapter 3 of *Laboratory Techniques in Biochemistry and Molecular Biology: Hybridization With Nucleic Acid Probes, part I. Theory and Nucleic Acid Preparation,* P. Tijssen, ed. elsevier, N.Y. (1993) and Chapter 3 of *Laboratory Techniques in Biochemistry and Molecular Biology: Gybridization With Nucleic Acid Probes, Part I. Theory and Nucleic Acid Preparation.* P. Tijssen ed. Elsevier, N.Y. (1993)).

In a preferred embodiment, the total nucleic acid is isolated from a given sample using, for example, an acid guanidinium-phenol-chloroform extraction method and poly $A^+$ mRNA is isolated by oligo dT column chromatography or by using (dT)n magnetic beads (see, e.g., Sambrook et al., *Molecular Cloning: A Laboratory Manual* 2nd ed.), Vols. 1–3, Cold Spring Harbor Laboratory, (1989), or *Current Protocols in Molecular Biology,* F. Ausubel et al., ed. Greene Publishing and Wiley-Interscience, New York (1987)).

Frequently, it is desirable to amplify the nucleic acid sample prior to hybridization. One of skill in the art will appreciate that whatever amplification method is used, if a quantitative result is desired, care must be taken to use a method that maintains or controls for the relative frequencies of the amplified nucleic acids.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high density array may then include probes specific to the internal standard for quantification of the amplified nucleic acid.

One preferred internal standard is a synthetic AW106 cRNA. The AW106 cRNA is combined with RNA isolated from the sample according to standard techniques known to those of skill in the air. The RNA is then reverse transcribed using a reverse transcriptase to provide copy DNA. The cDNA sequences are then amplified (e.g., by PCR) using labeled primers. The amplification products are separated, typically by electrophoresis, and the amount of radioactivity (proportional to the amount of amplified product) is determined. The amount of mRNA in the sample is then calculated by comparison with the signal produced by the known AW106 RNA standard. Detailed protocols for quantitative PCR are provided in *PCR Protocols, A guide to Methods and Applications,* Innis et al., Academic Press, Inc. N.Y., (1990).

Other suitable amplification methods include, but are not limited to polymerase chain reaction (PCR) (Innis et al., (1990) *PCR Protocols, A guide to Methods and Application,* Academic Press, Inc. San Diego), ligase chain reaction (LCR) (see Wu and Wallace (1989) *Genomics* 4: 560, Landegren et al. (1988) *Science* 241: 1077, and Barringer et al. (1990) *Gene* 89: 117, transcription amplification (Kwoh et al. (1989) *Proc. Natl. Acad. Sci. USA* 86: 1173), and self-sustained sequence replication (Guatelli et al. (1990) *Proc. Nat. Acad. Sci. USA* 87: 1874).

ii) Hybridization Assays

A variety of methods for specific DNA and RNA measurement using nucleic acid hybridization techniques are known to those of skill in the art (see Sambrook et al. Supra). For example, one method for evaluating the presence, absence, or quantity of DNA encoding suppressor of fused proteins in a sample involves a Southern transfer. Briefly, the digested genomic DNA is run on agarose slab gels in buffer and transferred to membranes.

Hybridization is carried out using the nucleic acid probes specific for the target suppressor of fused sequence or subsequence. Nucleic acid probes are designed based on the nucleic acid sequences encoding suppressor of fused proteins (see SEQ ID NO: 2). The probes can be full length of the nucleic acid sequence encoding the suppressor of fused protein. Shorter probes are empirically tested for specificity. Preferably nucleic acid probes are 20 bases or longer in length. (See Sambrook et al. For methods of selecting nucleic acid probe sequences for use in nucleic acid hybridization.) Visualization of the hybridized portions allows the qualitative determination of the presence or absence of DNA encoding suppressor of fused proteins.

Similarly, a Northern transfer may be used for the detection of mRNA encoding suppressor of fused proteins. In brief the mRNA is isolated from a given cell sample using, for example, and acid guanidinium-phenol-chloroform extraction method. The mRNA is then electrophoresed to separate the mRNA species and the mRNA is transferred from the gel to a nitrocellulose membrane. As with the Southern blots, labeled probes are used to identify the presence or absence of suppressor of fused proteins.

A variety of nucleic acid hybridization formats are known to those skilled in the art. For example, common formats include sandwich assays and competition or displacement assays. Hybridization techniques are generally described in "*Nucleic Acid Hybridization, A Practical Approach,*" Ed. Hames, B. D. and Higgins, S. J., IRL Press, (1985); Gall and Pardue *Proc. Natl. Acad. Sci. U.S.A.* 63: 378–383 (1969); and John et al. *Nature* 223: 582–587 (1969).

For example, sandwich assays are commercially useful hybridization assays for detecting or isolating nucleic acid sequences. Such assays utilize a "capture" nucleic acid covalently immobilized to a solid support and a labeled "signal" nucleic acid in solution. The clinical sample will provide the target nucleic acid. The "capture" nucleic acid and "signal" nucleic acid probe hybridize with the target nucleic acid to form a "sandwich" hybridization complex. To be effective, the signal nucleic acid cannot hybridize with the capture nucleic acid.

Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P-labelled probes or the like. Other labels include ligands which bind to labeled antibodies, fluorophores, chemiluminescent agents, enzymes, and antibodies which can serve as specific binding pair members for a labeled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal.

The label may also allow indirect detection of the hybridization complex. For example, where the label is a hapten or antigen, the sample can be detected by using antibodies. In these systems, a signal is generated by attaching fluorescent or enzyme molecules to the antibodies or, in some cases, by attachment to a radioactive label. (Tijssen, P., "Practice and Theory of Enzyme Immunoassays," *Laboratory Techniques in Ciochemistry and Molecular Biology,* Burdon, R. H., van Knippenberg, P. H., Eds., Elsevier (1985), pp. 9–20.).

The sensitivity of the hybridization assays may be enhanced through use of a nucleic acid amplification system which multiplies the target nucleic acid being detected. Examples of such systems include the polymerase chain reaction (PCR) system and the ligase chain reaction (LCR) system. Other methods recently described in the art are the nucleic acid sequence based amplification (NASBA™, Cangene, Mississauga, Ontario) and Q Beta Replicase systems.

An alternative means for determining the level of expression of a gene encoding a suppressor of fused protein is in situ hybridization. In situ hybridization assays are well known and are generally described in Angerer, et al., *Methods Enzymol.,* 152: 649–660 (1987). In an in situ hybridization assay, cells or tissue specimens are fixed to a solid support, typically a glass slide. If DNA is to be probed, the cells are denatured with heat or alkali. The cells are then contacted with a hybridization solution at a moderate temperature to permit annealing of labeled probes specific to suppressor of fused proteins. The probes are preferably labeled with radioisotopes of fluorescent reporters.

iii) Amplification Based Assays

In another embodiment, the suppressor of fused gene or gene product call be detected (assayed) using an amplification based assay. In an amplification based assay, all or part of the suppressor of fused gene or transcript (e.g., mRNA or cDNA) is amplified and the amplification product is then detected. Where there is no underlying gene or gene product to act as a template amplification is non-specific or non-existent and there is no single amplification product. Where the underlying gene or gene product is present, the target sequence is amplified providing an indication of the presence, absence, or quantity of the underlying gene or mRNA.

Amplification-based assays are well known to those of skill in the art (see, e.g., Innis, supra.). The cDNA sequence provided for the suppressor of fused gene is sufficient to enable one of skill to routinely select primers to amplify any portion of the gene.

Amplification primers can be selected to provide amplification products that span specific deletions, truncations, and insertions, thereby facilitating the detection of specific abnormalities.

iv) Specific Detection of Abnormalities (e.g., Mutations)

Abnormal suppressor of fused genes or gene products are characterized by premature stop codons, deletions, insertions or change of particular amino acids. Premature stop codons and deletions can be detected by decreased size of the gene or gene product (mRNA transcript or cDNA). Similarly, insertions can be detected by increased size of the gene or gene product. Alternatively, mutations can be determined by sequencing of the gene or gene product according to standard methods.

In addition, amplification assays and hybridization probes can be selected to specifically target particular abnormalities. For example, where the abnormality is a deletion, nucleic acid probes or amplification primers can be selected that specifically hybridize to or amplify, respectively, the nucleic acid sequence that is deleted in the abnormal gene. The probe will fail to hybridize, or the amplification reaction will fail to provide specific amplification, to abnormal versions of the suppressor of fused nucleic acids which have the deletion. Alternatively, the probe or amplification reaction can be designed to span the entire deletion or either end of the deletion (deletion junction). Similarly, probes and amplification primers can be selected that specifically target point mutations or insertions. Methods for detecting specific mutations were described in, for example, U.S. Pat. No. 5,512,441. In the case of PCR amplification primers can be designed to hybridize to a portion of the suppressor of fused gene but the terminal nucleotide at the 3' end of the primer can be used to discriminate between the mutant and wild-type forms of suppressor of fused gene. If the terminal base matches the point mutation or the wild-type sequence, polymerase dependent extension can proceed and an amplification product is detected. This method for detecting point mutations or polymorphisms was described in detail by Sommer et al., (1989) *Mayo Clin. Proc.* 64:1361–1372. By using appropriate controls, one can develop a kit having both positive and negative amplification products. The products can be detected using specific probes or by simply detecting their presence or absence. A variation of the PCR method uses LCR where the point of discrimination, i.e., either the point mutation or the wild-type bases fall between the LCR oligonucleotides. The ligation of the oligonucleotides becomes the means for discriminating between the mutant and wild-type forms of the suppressor of fused gene.

A variety of automated solid-phase detection techniques are also appropriate for detecting the presence or absence of mutations in the suppressor of fused gene. For instance, very large scale immobilized polymer arrays (VLSIPS™), available from Affymetrix, Inc. In Santa Clara, Calif. are used for the detection of nucleic acids having specific sequences of interest. See, Fodor et al. (1991) *Science,* 251: 767–777; Sheldon et al. (1993) *Clinical Chemistry* 39(4): 718–719. and Kozal et al. (1996) *Natural Medicine* 2(7): 753–759. For example, oligonucleotides that hybridize to all known suppressor of fused mutations can be synthesized on a DNA chip (such chips are available from Affymetrix) and the nucleic acids from samples hybridized to the chip for simultaneous analysis of the sample nucleic acid for the presence or absence of any of the known suppressor of fused mutations. Protocols for detecting mutations are also described in, for example, Tijssen (1993) *Laboratory Techniques in biochemistry and molecular biology— hybridization with nucleic acid probes parts I and II,* Elsevier, New York, and Choo (ed) (1994) *Methods In Molecular Biology* Volume 33-*In situ Hybridization Protocols,* Humana Press Inc., New Jersey (see also, other books in the *Methods in Molecular Biology* series).

v) Detection of Expression Levels

Where it is desired to quantify the transcription level (and thereby expression) of normal or mutated suppressor of fused genes in a sample, the nucleic acid sample is one in which the concentration of the mRNA transcript(s) of the suppressor of fused gene, or the concentration of the nucleic acids derived from the mRNA transcrip(s), is proportional to the transcription level (and therefore expression level) of that gene. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear. Thus, for example, an assay where a 5 fold difference in concentration of the target mRNA results in a 3 to 6 fold difference in hybridization intensity is sufficient for most purposes. Where more precise quantification is required appropriate controls can be run to collect for variations introduced in sample preparation and hybridization as described herein. In addition, serial dilutions of "standard" target mRNAs can be used to prepare calibration curves according to methods well known to those of skill in the art. Of course, where simple detection of the presence or absence of a transcript is desired, no elaborate control or calibration is required.

C) Polypeptide Assays

The expression of the human suppressor of fused gene can also be detected and/or quantified by detecting or quantifying the expressed suppressor of fused polypeptide. The suppressor of fused polypeptides can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitating reactions, immunodiffusion (single or double), immunoelectrophoresis, radioimmunoassay(RIA), enzyme-linked immunosorbent assays (ELISAs), immunofluorescent assays, Western blotting, and the like.

In a particularly preferred embodiment, the suppressor of fused polypeptides are detected in an electrophoretic protein separation, more preferably in a two-dimensional electrophoresis, while in a most preferred embodiment, the suppressor of fused polypeptides are detected using a immunoassay.

As used herein, an immunoassay is an assay that utilizes an antibody to specifically bind to the analyte (suppressor of fused polypeptide). The immunoassay is thus characterized by detection of specific binding of a suppressor of fused polypeptide to an anti-suppressor of fused antibody as opposed to the use of other physical or chemical properties to isolate, target, and quantify the analyte.

1) Electrophoretic Assays

As indicated above, the presence or absence of suppressor of fused polypeptides in a biological sample can be determined using electrophoretic methods. Means of detecting proteins using electrophoretic techniques are well known to those of skill in the art (see generally, R. Scopes (1982) *Protein Purification,* Springer-Verlag, N.Y.; Deutscher, (1990) *Methods in Enzymology Vol.* 182: *Guide to Protein Purification.,* Academic Press, Inc., N.Y.).

2) Immunological Binding Assays

In a preferred embodiment, the suppressor of fused polypeptides are detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology Volume* 37: *antibodies in Cell Biology,* Asain, ed. Academic Press, Inc. New York (1993); *Basic and Clinical Immunology* 7th Edition, Stites & Terr, eds. (1991). Immunological binding assays (or immunoassays) typically utilize a "capture agent" to specifically bind to and often immobilize the analyte (in this case suppressor of fused polypeptide or subsequence). The capture agent is a moiety that specifically binds to the analyte. In a preferred embodiment, the capture agent is an antibody that specifically binds suppressor of fused polypeptide(s). The antibody (anti-suppressor of fused) may be produced by any of a number of means well known to those of skill in the art as described above in Section III(A).

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled suppressor of fused polypeptide or a labeled anti-suppressor of fused antibody. Alternatively, the labeling agent may be a third moiety, such as another antibody, that specifically binds to the antibody/suppressor of fused complex.

In a preferred embodiment, the labeling agent is a second human suppressor of fused antibody bearing a label. Alternatively, the second suppressor of fused antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme labeled streptavidin.

Other proteins capable of specifically binding immunoglobulin constant regions, such as protein A or protein G, may also be used as the label agent. The protein are normal constituents of the cell walls of strepococcal bacteria. They exhibit a strong non-immunogenic reactivity with immunoglobulin constant regions from a variety of species (see, generally Kronval, et al. (1973) *J. Immunol.,* 111: 1401–1406, and Akerstrom, et al. (1985) *J. Immunol.,* 135:2589–2542). Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10° C. to 40° C.

a) Non-Competitive Assay Formats

Immunoassays for detecting suppressor of fused polypeptide may be either competitive or noncompetitive. Noncompetitive immunoassays are assays in which the amount of captured analyte (in this case suppressor of fused) is directly measured. In one preferred "sandwich" assay, for example, the capture agent (anti-suppressor of fused antibodies) can be bound directly to a solid substrate where the are immobilized. These immobilized antibodies then capture suppressor of fused present in the test sample. The suppressor of fused thus immobilized in then bound by a labeling agent, such as a second human suppressor of fused antibody bearing a label. Alternatively, the second suppressor of fused antibody may lack a label, but it may, in turn, be bound by a labeled third antibody specific to antibodies of the species from which the second antibody is dervied. The second can be modified with a detectable moiety, such as biotin, to which a third labeled molecule can specifically bind, such as enzyme-labeled streptavidin.

b) Competitive Assay Formats

In competitive assays, the amount of analyte (suppressor of fused) present in the sample is measured indirectly by measuring the amount of an added (exogenous) analyte (suppressor of fused) displaced (or competed away) from a capture agent (anti-suppressor of fused antibody) by the analyte present in the sample. In one competitive assay, a known amount of, in this case, suppressor of fused is added to the sample and the sample is then contacted with a capture agent, in this case an antibody that specifically bind suppressor of fused. The amount of suppressor of fused bound to the antibody is inversely proportional to the concentration of suppressor of fused present in the sample.

In a particularly preferred embodiment, the antibody is immobilized on a solid substrate. The amount of suppressor of fused bound to the antibody may be determined either by measuring the amount of suppressor of fused present in a suppressor of fused/antibody complex, or alternatively by measuring the amount of remaining uncomplexed suppressor fused. The amount of suppressor of fused may be detected by providing a labeled suppressor of fused molecule.

A hapten inhibition assay is another preferred competivite assay. In this assay a known analyte, in this case suppressor of fused is immobilized on a solid substrate. A known amount of anti-suppressor of biased antibody is added to the sample, and the sample is then contacted with the immobilized suppressor of fused. In this case, the amount of anti-suppressor of fused antibody bound to the immobilized suppressor of fused is inversely proportional to the amount of suppressor of fused present in the sample. Again the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

c) Other Assay Formats

In a particularly preferred embodiment, Western blot immunoblot analysis is used to detect and quantify the presence of suppressor of fused in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind suppressor of fused. The anti-suppressor of fused antibodies specifically bind to suppressor of fused on the solid support. These antibodies may be directly labeled or alternatively may be subsequently detected using labeled antibodies (e.g., labeled sheep anti-mouse antibodies) that specifically bind to the anti-suppressor of fused.

Other assay formats include liposome immunoassays (LIA), which use liposomes designed to bind specific molecules (e.g., antibodies) and release encapsulated reagents or markers. The released chemicals are then detected according to standard techniques (see, Monroe et al. (1986) *Amer. Clin. Prod. Rev.* 5:34–41).

d) Scoring of the Assay

The assays of this invention are scored (as positive or negative for suppressor of fused polypeptide) according to standard methods well known to those of skill in the art. The particular method of scoring will depend on the assay format and choice of label. For example, a Western Blot assay can be scored by visualizing the colored product produced by the enzymatic label. A clearly visible colored band or spot at the collect molecular weight is scored as a positive result, while the absence of a clearly visible spot or band is scored as a negative. In a preferred embodiment, a positive test will show a signal intensity (e.g., suppressor of fused polypeptide quantity) at least twice that of the background and/or control and more preferably at least 3 times or even at least 5 times greater than the background and/or negative control.

e) Reduction of Non-specific Binding

One of skill in the art will appreciate that it is often desirable to reduce non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this involves coating the substrate with a proteinaceous composition. In particular, protein compositions such as bovine serum albumin (BSA), nonfat powdered milk, and gelatin are widely used with powdered milk being most preferred.

f) Labels

The particular label or detectable group used in the assay is not a critical aspect of the invention, so long as it does not significantly interfere with the specific binding of the antibody used in the assy. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., Dynabeads™), fluorescent dyes (e.g., fluorescein isothocyanate, texas red, rhodamine, and the like), radiolabels (e.g. $^3$H, $^{125}$P, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

The label may be coupled directly or indirectly to the desired component of the assay according to methods well known in the art. As indicated above, a wide variety of labels may be used, with the choice of label depending oil sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody. The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophtalazinediones, e.g., luminol. For a review of various labeling or signal producing systems which may be used, see, U.S. Pat. No. 4,391,904).

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

g) Substrates

As mentioned above, depending upon the assay, various components, including the antigen, target antibody, or anti-human antibody, may be bound to a solid surface. Many methods for immobilizing biomolecules to a variety of solid surfaces are known in the art. For instance, the solid surface may be a membrane (e.g., nitrocellulose), a mictrotiter dish (e.g., PVC, polypropylene, or polystyrene), a test tube (glass or plastic), a dipstick (e.g., glass, PVC, polypropylene, polystyrene, latex and the like), a microcentrifuge tube, or a glass or plastic bead. The desired component may be covalently bound or noncovalently attached through non-specific bonding.

A wide variety of organic and inorganic polymers, both natural and synthetic, may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed include paper, glasses, ceramics, metals, metalloids, semiconductive materials, cements or the like. In addition, are included substances that form gels, such as proteins (e.g., gelatins) lipopolysaccharides, silicates, agarose and polyacrylamides can be used. Polymers which form several aqueous phases, such as dextrans, polyalkylene glycols or surfactants, such as phospholipids, long chain (12–24 carbon atoms) alkyl ammonium salts and the like are also suitable. Where the solid surface is porous, various pore sizes may be employed depending upon the nature of the system.

In preparing the surface, a plurality of different materials may be employed, particularly as laminates, to obtain various properties. For example, protein coatings, such as gelatin can be used to avoid non-specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. See, for example, *Immobilized Enzymes,* Ichiro Chibata, Halsted Press, New York, 1978, and Cuatrecasas (1970) *J. Biol. Chem.* 245 3059).

In addition to covalent bonding, various methods for noncovalently binding an assay component can be used. Noncovalent binding is typically nonspecific absorption of a compound to the surface. Typically, the surface is blocked with a second compound to prevent nonspecific binding of labeled assay components. Alternatively, the surface is designed such that is nonspecifically binds one component but does not significantly bind another. For example, a surface bearing a lectin such as Concanavalin A will bind a carbohydrate containing compound but not a labeled protein that lacks glycosylation. Various solid surfaces for use in noncovalent attachment of assay components are reviewed in U.S. Pat. Nos. 4,447,576 and 4,254,082.

D) Evaluation of Suppressor of Fused Expression Levels and/or Abnormal Expression One of skill will appreciate that abnormal expression levels or abnormal expression products (e.g., mutated transcripts, truncated or non-sense polypeptides) are identified by comparison to normal expression levels and normal expression products. Normal levels of expression or normal expression products can be determined for any particular population, subpopulation, or group of organisms according to standard methods well known to those of skill in the art. Typically this involves identifying healthy organisms (i.e. organisms without suppressor of fused or basal cell carcinomas) and measuring expression levels of the suppressor of suppressor of fused gene (as described herein) or sequencing the gene, mRNA, or reverse transcribed cDNA, to obtain typical (normal) sequence variations. Application of standard statistical methods used in molecular genetics permits determination of baseline levels of expression, and normal gene products as well as significant deviations from such baseline levels.

E. Detection Kits

The present invention also provides for kits for the diagnosis of organisms (e.g., patients). The kits preferably include one or more reagents for determining the presence or absence of the suppressor of fused gene, for quantifying expression of the fused gene, or for detecting an abnormal suppressor of fused gene or expression products of an abnormal suppressor of fused gene. Preferred reagents include nucleic acid probes that specifically bind to the normal suppressor of fused gene, cDNA, or subsequence thereof, probes that specifically bind to abnormal suppressor of fused gene (e.g., suppressor of fused containing premature truncations, insertions, or deletions), antibodies that specifically bind to normal suppressor of fused polypeptides or subsequences thereof, or antibodies that specifically bind to abnormal suppressor of fused polypeptides or subsequences thereof. The antibody or hybridization probe may be free or immobilized on a solid support such as a test tube, a microtiter plate, a dipstick and the like. The kit may also contain instructional materials teaching the use of the antibody or hybridization probe in an assay for the detection of a deviation from the normal sequence of a suppressor of fused gene.

The kits may include alternatively, or in combination with any of the other components described herein, an anti-suppressor of fused antibody. The antibody can be monoclonal or polyclonal. The antibody can be conjugated to another moiety such as a label and/or it can be immobilized on a solid support (substrate).

The kits(s) may also contain a second antibody for detection of polypeptide/antibody complexes according to the invention or for detection of hybridized nucleic acid probes. The kit may contain appropriate reagents for detection of labels, positive and negative controls, washing solutions, dilution buffers and the like.

VI

Modulation of Expression of Suppressor of Fused Genes

In still another embodiment, this invention provides methods of regulating the expression of endogenous suppressor of fused genes. The expression of a suppressor of fused gene product may be increased. Regulation of suppressor of fused gene may provide a convenient and controllable model system for the study of the HH-PTC pathway, especially in human beings.

Methods of altering the expression of endogenous genes are well known to those of skill in the art. Typically such methods involve altering or replacing all or a portion of the regulatory sequences controlling expression of the particular gene that is to be regulated. In a preferred embodiment, the regulator)y sequences (e.g., the native promoter) upstream of the suppressor of fused gene is altered.

This is typically accomplished by the use of homologous recombination to introduce a heterologous nucleic acid into the native regulatory sequences. To downregulate expression the suppressor of fused gene product, simple mutations that either alter the reading frame or disrupt the promoter are suitable. To upregulate expression of the suppressor of fused gene product, the native promoter(s) can be substituted with heterologous promoter(s) that induce higher than normal levels of transcription.

In a particularly preferred embodiment, nucleic acid sequences comprising the structural gene in question or upstream sequences are utilized for targeting heterologous recombination constructs. Upstream and downstream sequences can be readily determined using the information provided herein. Such sequences, for example, can be extended using 5'- or 3'-RACE and homologous recombination constructs created with only routine experimentation.

The use of homologous recombination to alter expression of endogenous genes is described in detail in U.S. Pat. No. 5,272,071, WO 91/09955, WO 93/09222, WO 96/2941 1, WO 95/31560, and WO 91/12650.

A) Pharmaceutical Compositions

The proteins, polypeptides, antibodies and anti-suppressor of fused antibody-effector (e.g., enzyme toxin, hormone, growth factor, drug,, etc.) conjugates or fusion proteins of this invention are useful for parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the polypeptides and related compounds described of, when administered orally, must be protected from digestion. This is typically accomplished either by complexing the protein with a composition to render it resistant to acidic and enzymatic hydrolysis or by packaging the protein in an appropriately resistant carrier such as a liposome. Means of protecting proteins from digestion are well known in the art.

The pharmaceutical compositions of this invention are useful for topical administration. In another embodiment, the compositions are useful for parenteral administration, such as intravenous administration or administration into a body cavity or lumen of an organ. The compositions for administration will commonly comprise a solution of the polypeptide, antibody or antibody chimera/fusion dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of chimeric molecule in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Substantially higher dosages are possible in topical administration. Actual methods for preparing parenterally administrable compositions will be known or apparent to those skilled in the art and are described in more detail in such publications as *Remington's Pharmaceutical Science, 15th*., Mack Publishing Company, Easton, Pa. (1980).

The compositions containing the present polypeptides, antibodies or antibody chimer/fusion, or a cocktail therof (i.e., with other proteins), can be administered for therapeutic treatments. In therapeutic applications, compositions are administered to a patient suffering from a disease in an amount sufficient to cure or at least partially arrest the disease and its complications. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the proteins of this invention to effectively heat the patient.

B) Cellular Transformation and Gene Therapy

The present invention provides packageable human suppressor of fused nucleic acids (cDNAs) for the transformation of cells in vitro and in vivo. These packageable nucleic acids can be inserted into any of a number of well known vectors for the transfection and transformation of target cells and organisms as described below. The nucleic acids are transfected into cells, ex vivo or in vivo, through the interaction of the vector and the target cell. The suppressor of fused cDNA, under the control of a promoter, then expresses the suppressor of fused protein thereby mitigating the effects of absent suppressor of fused genes or partial inactivation of the suppressor of fused gene or abnormal expression of the suppressor of fused gene.

Such gene therapy procedures may be useful to connect acquired and inherited genetic defects, especially "Split hand/Split foot Malformation Type 3" (SHFM3), possibly cancer, and viral infection in a number of contexts. The ability to artificial genes in humans facilitates the prevention and/or cure of many important human diseases, including many diseases which are not amenable to treatment by other therapies. As an example, in vitro expression of cholesterol-regulating genes, genes which selectively block the replication of HIV, and tumor-suppressing genes in human patients dramatically improves the treatment of heart disease, AIDS, and cancer, respectively. For a review of gene therapy procedures, see Anderson, *Science* (1992) 256:808–813; Nabel and Felgner (1993) *TIBTECH* 11: 211–217; Mitani and Caskey (1993) *TIBTECH* 11: 162–166; Mulligan (1993) *Science* 926–932; Dillon (1993) *TIBTECH* 11: 167–175; Miller (1992) *Nature* 357: 455–460; Van Brunt (1988) *Biotechnology* 6(10): 1149–1154; Vigne (1995) *Restorative Neurology and Neuroscience* 8: 35–36; Kremmer and Perricaudet (1995) *British Medical Bulletin* 51(1) 31–44; Haddada et al. (1995) in *Current Topics in Microbiology and Immunology* Doerfler and Böhm (eds) Springer-Verlag, Heidelberg Germany; and Yu et al, *Gene Therapy*(1994) 1:13–26.

Delivery of the gene or genetic material into the cell is the first critical step in gene therapy treatment of disease. A large number of delivery methods are well known to those of skill in the art. Such methods include, for example liposome-based gene delivery (Debs and Zhu (1993) WO 93/24640; Mannino and Gould-Fogerite (1988) *BioTechniques* 6(7): 682–691; Rose U.S. Pat No. 5,279,833; Brigham (1991) WO 91/06309; and Felgner et al. (1987) *Proc. Natl. Acad. Sci. USA* 84: 7413–7414), and replication-defective retroviral vectors harboring a therapeutic polynucleotide sequence as part of the retroviral genome (see, e.g., Miller et al. (1990) *Mol. Cell. Biol.* 10:4239 (1990; Kolberg (1992) *J. NIH Res.* 4:43, and Cornetta et al. *Hum. Gene Ther.* 2:215 (1991)). Widely used retroviral vectors include those based upon murine leukemia virus (MuLV), gibbon ape leukemia virus (GaLV), Simian Immuno deficiency virus (SIV), human immuno deficiency virus (HIV), and combinations thereof. See, e.g., Buchscher et al. (1992) *J. Virol.* 66 (5) 2731–2739; Johann et al. (1992) *J. Virol.* 66 (5): 1635–1640 (1992); Sommerfelt et al., (1990) *Virol.* 176:58–59; Wilson et al. (1989) *J. Virol.* 63:2374–2378; Miller et al., *J. Virol.* 65:2220–2224 (1991); Wong-Staal et al., PCT/US94/05700, and Rosenburg and Fauci (1993) in *Fundamental Immunology, Third Edition* Paul (ed) Raven Press, Ltd., New York and the references therein, and Yu et al., *Gene Therapy* (1994) supra).

AAV-based vectors are also used to transduce cells with target nucleic acids, e.g., in the in vitro production of nucleic acids and peptides, and in in vivo and ex vivo gene therapy procedures. See, West et al. (1987) *Virology* 160:38–47; Carter et al. (1989) U.S. Pat. No. 4,797,368; Carter et al. WO 93/24641 (1993); Kotin (1994) *Human Gene Therapy*

5:793–801; Myzyczka (1994) *J. Clin. Invest* 94:1351 and Samulski (supra) for an overview of AAV vectors. Construction of recombinant AAV vectors are described in a number of publications, including Lebkowski, U.S. Pat. No. 5,173,414; Tratschin et al. (1985) *Mol. Cell. Biol.* 5(11):3251–3260; Tratschin, et al. (1984) *Mol. Cell. Biol.* 4:2072–2081; Hermonat and Muzyczka (1984) *Proc. Nalt. Acad. Sci. USA* 81:6466–6470; McLaughlin et al. (1988) and Samulski et al. (1989) *J. Virol.* 63:03822–3828. Cell lines that can be transformed by rAAV include those described in Lebkowski et al. (1988) *Mol. Cell. Biol.* 8:3988–3996.

VII

A) Ex vivo Transformation of Cells

Ex vivo cell transformation for diagnostics, research, or for gene therapy (e.g., via re-infusion of the transformed cells into the host organism) is well known to those of skill in the art. In a preferred embodiment, cells are isolated from the subject organism, transfected with the suppressor of fused gene or cDNA of this invention, and re-infused back into the subject organism (e.g., patient). Various cell types suitable for ex vivo transformation are well known to those of skill in the art. Particular preferred cells are progenitor or stem cells (see, e.g., Freshney et al. in *Culture of Animal Cells, a Manual of Basic Technique,* third edition Wiley-Liss, New York (1994)) and the references cited therein for a discussion of how to isolate and culture cells from patients).

As indicated above, in a preferred embodiment, the packageable nucleic acid encodes a suppressor of fused polypeptide under the control of an activated or constitutive promoter.

In one particularly preferred embodiment, stem cells are used in ex vivo procedures for cell transformation and gene therapy. The advantage to using stem cells is that they can be differentiated into other cell types in vivo, or can be introduced into a mammal (such as the donor of the cells) where they will engraft in the bone marrow. Methods for differentiating CD34$^+$ cells in vitro into clinically important immune cell types using cytokines such a GM-CSF, IFN-γ and TNF-α are known (see, Inaba et al. (1992) *J. Exp. Med.* 176: 1693–1702, and Szabolcs et al. (1995) 154: 5851–5861).

Stem cells are isolated for transduction and differentiation using known methods. For example, in mice, bone marrow cells are isolated by sacrificing the mouse and cutting the leg bones with a pair of scissors. Stem cells are isolated from bone marrow cells by panning the bone marrow cells with antibodies which bind unwanted cells, such as CD4$^+$ and CD8$^+$ (T cells), CD45$^+$ (panB cells), GR-1 (granulocytes), and la$^d$ (differentiated antigen presenting cells). For an example of this protocol see, Inaba et al. (1992) *J. Exp. Med.* 176: 1693–1702.

In humans, bone marrow aspirations from iliac crests are performed e.g., under general anesthesia in the operating room. The bone marrow aspirations is approximately 1,000 ml in quantity and is collected from the posterior iliac bones and crests. If the total number of cells collected is less than about 2×10$^8$/kg, a second aspiration using the sternum and anterior iliac crests in addition to posterior crests is performed. During the operation, two units of irradiated packed red cells are administered to replace the volume of marrow taken by the aspiration. Human hematopoietic progenitor and stem cells are characterized by the presence of a CD34 surface membrane antigen. This antigen is used for purification, e.g., on affinity columns which bind CD34. After the bone marrow is harvested, the mononuclear cells are separated from the other components by means of ficoll gradient centrifugation. This is performed by a semi-automated method using a cell separator (e.g., a Baxter Fenwal CS3000+ or Terumo machine). The light density cells, composed mostly of mononuclear cells are collected and the cells are incubated in plastic flasks at 37° C. for 1.5 hours. The adherent cells (monocytes, macrophages and B-Cells) are discarded. The non-adherent cells are then collected and incubated with a monoclonal anti-CD34 antibody (e.g., the murine antibody 9C5) at 4° C. for 30 minutes with gentle rotation.

The final concentration for the anti-CD34 antibody is 10 μg/ml. After two washes, paramagnetic microspheres (DynaBeads, supplied by Baxter Immunotherapy Group, Santa Ana, Calif.) coated with sheep antimouse IgG (Fc) antibody are added to the cell suspension at a ratio of 2 cells/bead. After a further incubation period of 30 minuter at 4° C., the rosetted cells with magnetic beads are collected with a magnet. Chymopapain (supplied by Baxter Immunotherapy Group, Santa Ana, Calif.) at a final concentration 200 U/ml is added to release the beads from the CD34+ cells. Alternatively, and preferably, an affinity column isolation procedure can be used which binds to CD34, or to antibodies bound to CD34 (see, the examples below). See, Ho et al. (1995) *Stem Cells* 13 Usuppl. 3): 100–105. See also, Brenner (1993) *Journal of hematotherapy* 2: 7–17. In another embodiment, hematopoietic stem cells are isolated from fetal cord blood. Yu et al. (1995) *Proc. Natl. Acad. Sci. USA* 92: 699–703 describe a preferred method of transducing CD34$^-$ cells from human fetal cold blood using retroviral vectors.

B) In vivo Transformation

Vectors (e.g., retroviruses, adenoviruses, liposomes, etc.) containing therapeutic nucleic acids can be administered directly to the organism for transduction of cells in vitro. Administration is by any of the routes normally used for introducing a molecule into ultimate contact with blood or tissue cells. The packaged nucleic acids are administered in any suitable manner, preferably with pharmaceutically acceptable carriers. Suitable methods of administering such packaged nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

Formulations suitable for oral administration can consist of (a) liquid solutions, such as an effective amount of the packagecd nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art.

The packaged nucleic acids, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the packaged nucleic acid with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, bluffers, bacteriostats, and solutes that render the formulation isotonic with the blood of the intended recipients and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of packaged nucleic acid can be presented in unit-dose or multi-dose sealed containers, such as ampules and vials. Injection solutions and suspensions can be prepared from sterile powders, granules, and tablets of the kind previously described. Cells transduced by the packaged nucleic acid as described above in the context of ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in treatment or prophylaxis, the physician evaluates circulating plasma levels of the vector, vector toxicities, progression of the disease, and the production of anti-vector antibodies. For administration, inhibitors and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

In a preferred embodiment, prior to infusion, blood samples are obtained and saved for analysis. Between $1 \times 10^8$ and $1 \times 10^{12}$ transduced cells are infused intravenously over 60–200 minutes. Vital signs and oxygen saturation by pulse oximetry are closely monitored. Blood samples are obtained 5 minutes and 1 hour following infusion and saved for subsequent analysis. Leukopheresis, transduction and reinfusion can be repeated are repeated every 2 to 3 months. After the first treatment, infusions can be performed on a outpatient basis at the discretion of the clinician. If the reinfusions is given as an outpatient, the participant is monitored for at least 4, and preferably 8 hours following the therapy. Transduced cells are prepared for reinfusion according to established methods. See, Abrahamsen et al. (1991) *J. Clin. Apheresis,* 6: 48–53; Carter el al. (1988) *J. Clin. Apheresis,* 4:113–117; Aebersold et al. (1988) *J. Immunol Meth.,* 112: 1–7; Muul et al. (1987) *J. Immunol. Methods* 101: 171–181 and Carter et al. (1987) *Transfusion* 27: 362–365. After a period of about 2–4 weeks in culture, the cells should number between $1 \times 10^8$ and $1 \times 10^{12}$. In this regard, the growth characteristics of cells vary from patient to patient and from cell type to cell type. About 72 hours prior to reinfusion of the transduced cells, an aliquot is taken for analysis of phenotype, and percentage of cells expressing the therapeutic agent.

EXAMPLES

Materials and Methods
Cloning of a Human SU(FU) Homolog

By searching the EST database a partial cDNA clone (GenBank Acc: AA223637) was identified having significant sequence identity with the drosophila SU(FU). The EST clone was sequenced in our laboratory verifying the presence of a poly A+tail in the 3' end. To obtain the missing 5' end, PCR primers were designed and used with the RACE technology on epidermal cDNA (Zaphiropoulos and Toftgard. DNA Cell Biology, 15, 1049–1056, 1996). The primes used were 5' GAA GCT GAT GTA CTG CCA GTG and 5' GCG TCG ACC TGG AGC GGG TTC GGC TGG T (nested primer).

The products of the RACE amplification were cloned into the pGEM 5 vector (Promega) and sequenced with dye-dideoxy nucleotides using the facilities of Cybergene AB.
Northern and Southern Blot Hybridization Multiple Tissue Northern Blots with human samples and Zoo Blots (Southern Blots with EcoRI-digested genomic DNA from various species) were obtained from Clontech. Total RNA from fibroblasts and primary keratinocytes (botgh prepared from healthy donors and grown for five passages) as well as transformed keratinocytes (HaCaT cells) were prepared as described. An Apal fragment of the human SUFUH clone corresponding to basepairs 1182–1630 was labelled with $^{32}$P using the Megaprime DNA labelling kit (Amersham, UK) and hybridized to these Blots. After stripping the blots with 1% SDS the amount and quality of the RNA was monitored with a probe specific for β-actin.
Whole Mount in situ Hybridization Digoxin-labelled riboprobes for the murine Su(fu) were prepared using the DIG RNA Labelling kit (Boehringer Mannheim, FRG) using the mouse Su(fu) EST as a template and Sp6 and T7 as primer's for sense- and intisense probe respectively. Timely mated NMRI mice were sacrificed and the embryos harvested, and after fixation with 4% paraformaldehyde whole mount in situ hybridization was performed according to standard procedures. The hybridizing probe was detected using the DIG Nucleic Acid Detection kit (Boehringer Mannheim). Unspecific binding of the probe was monitored by comparison of samples hybridized with sense and antisense-probes.
Epitope-tagged Constructs for Human Gli and SUFUH Using the full length cDNA clones for human Gli and SUFUH as templates and oligonucleotides as 5' PCT primers containing in this order a HindIII restriction site, a Kozak sequence, a methonine codon, the sequence of the epitope tag and the first nucleotides of the coding region of the cDNA, plasmids coding for SUFUH that is N-terminally labelled with the myc-epitope tag and for human Gli that is N-terminally labelled with a hemagglutinin tag were generated after ligation into the CMV-5 expression vector.

Reporter Gene Assays

The PTCH1 genomic region was cloned as described previously. A 4.3 kb fragment of the 5'-regulatory region was subcloned into the pGL3-Basic vactor (Promega, Madison, Wis.) upstream of the firefly luciferase reporter gene. It was demonstrated that this construct can mediate activation of the reporter gene in different cell lines in response to expression of GLI-1 and SHH.

Human 293 cells (kidney epithelial cell line) were obtained from ATCC and grown in DMEM supplemented with penicillin and streptomycin and 10% fetal bovine serum (GIBCO BRL, Grand Island, N.Y.). Cells were passaged to 24-well plates the day before the experiments and transfections were carried out with DNA complexed to the Superfect transfection reagent (Qiagen GmbH, Düsseldorf, Germany) according to the manufacturer's instructions. Control experiments with a lacZ-expressing plasmid established that the transient transfection efficiency was 10–20%, data not shown. Twenty four hours after transfection, the medium was removed and the cells were lysed in Somalyze lysis buffer (BioOrbit, Turku, Finland). Luciferase activity was determined on a BioOrbit 1250 Luminometer using BioOrbit Luciferin Substrate and ATP reagents according to manufacturer's instructions. The results from at least four experiments from two independent transfections were compiled.

Immunoprecipitations and Western Blotting

Lysates were prepared from a near-confluent 75 $cm^2$ flask of 293 cells 24 hrs after transfection in I.P. buffer (PBS, 1% Nonidet-P40, 10 $\mu$M Pepstatin, 10 $\mu$M Aprotonin, 10 $\mu$M leupeptin and 1 mM PMSF). Immunoprecipitations were performed in I.P. buffer using 2 ul pf anti-HA and 20 ul of packed protein G plus/protein A agarose or 50 ul of agarose conjugated anti-myc beads. After binding for 1 hr at 4 degrees Celsius the beads were washed four times with 1 ml of I.P. buffer and eluted with SDS-PAGE sample buffer and the eluate was analysed. Immunoprecipitates as well as aliquots of lysates were separated on 7% SDS-PAGE, transferred to PVDF membrane (Millipore), and incubated with a 1:500 dilution of anti-HA or anti-myc antibody. Anti-myc antibody was directly conjugted to horseradish peroxidase (HRP) whereas in the case of anti-HA, a secondary HRP-conjugated antibody was used. Following second washes, enhanced chemiluminescence (Pierce) was performed according to the manufacturer's instructions.

Immunofluorescence 293 cells grown on teflon coated slides in 14 mm wells were fixed for 3 min in methanol at −20° C., then blocked PBSTX (PBS, 0,05% TX-100, 10% goat serum). All antibody labellings were for 1 hr in PBSTX at room temperature. Rabbit polyclonal and mouse monoclonals were detected with fluorescein-conjugated secondary antibodies.

Results

Cloning of SUFUH

By searching the EST database for genes homologous to the Drosophila melanogaster suppressor of fused (su(fu)), we found two EST clones partially encoding human and murine homologs. Starting with the human EST the full length cDNA was cloned by the RACE technology.

The full length cDNA of SUFUH has a size of 2239 base with an open reading frame of 484 amino acids starting at nucleotide 167 and ending at nucleotide 1619. The sequence of the protein shows no striking homology to any other protein described so far and demonstrates 40% identity and 61% similarity to the Drosophila melanogaster sequence (FIG. 1A). The similarity was not evenly distributed over the sequence. The PEST motif in the Drosophila protein is missing in the human counterpart. On the other hand, a duplicate octamer with only small amino acids (PGPTAPPA/PGPTAPPA) of no obvious function exists only in the human (amino acids 10–25), and not in the Drosophila molecule. Amino acids 3 1–124 of the human sequence are 66% identical to the Drosophila sequence whereas the remaining part has an identity of 32%. On the protein level, the murine Su(fu) sequence is 98% identical to the human sequence.

Expression of Mammalian SU(fu) in Adult Tissues and Conservation Among Species

SUFUH was expressed in all adult human tissues tested (FIG. 1B). There were two detected mRNAs one of 2,8 kb, predominant however was a band with a size of 6 kb. We also found both these messages in total RNA extracted from untransformed fibroplast and keratinocytes, but not in transformed keratinocytes (HaCaT). Since we found both messages with a probe against the coding region as well as the 3'-untranslated region, the two bands might be due to alternatively used polyadenylation signals. However, at present, we can not exclude alternative splicing of coding exons either. By hybridizing a Zoo Blot with the same probe we detected reactivity of comparable intensity with genomic DNA from six mammalian and one avian species, but not from yeast (data not shown).

Expression of Su(fu) in Embryonic Mouse Tissues

Figure 2B:
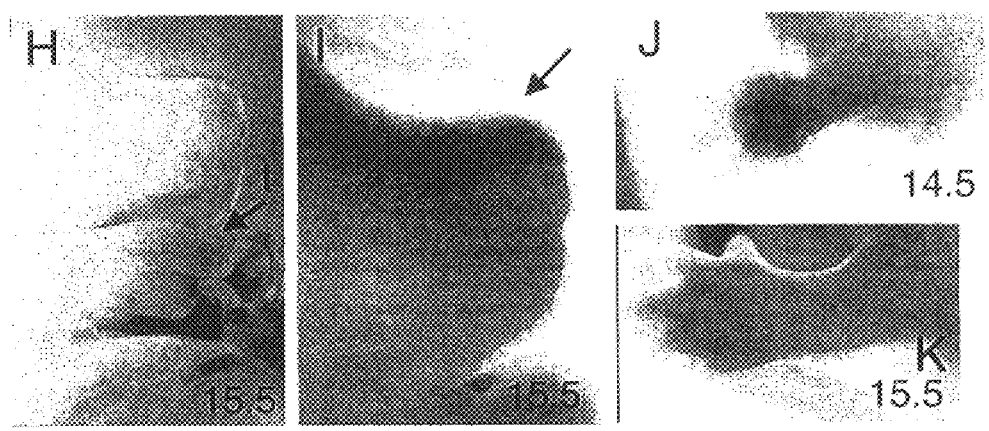

By whole mount in situ hybridization we investigated the expression of Su(fu) on NMRI mouse embryos of day post coitum (dpc) d.5 through 15.5. Through the entire period, we observed staining in the neutral tube (FIG. 2A) and later in its derivatives brain and spinal cord (C). Like Su(fu), Gli and Shh are expressed in neural tissues through their entire development, and their role in induction of various types of neurons was shown ([Hynes, 1997). The involvement of Gli-3 has also been shown by deficiencies in the forebrain development of the Gli-3-defective mutant extratoes (Xt) mice. The somites were also stained through the entire observation period, with initially the entire somites (FIGS. 2A, B, C) and from dpc 12.5 ohe the sclerotome (FIG. 2D) and the sclrerotome-dervied vertebrae were also stained. Shh has been shown to induce the sclerotome marker Pax-1 and Gli-2 and Gli-3 mutations have defferent effects on skeletal development. In birds different Gli isoforms lead to the induction of myotome and sclerotome of the somite ([Borycki, 1998]). From dpc 13.5 we could as well observe signals in the tissue adjacent to the chondrifying ribs (FIG. 2F). Even the expression of Su(fu) during rib formation was not unexpected since gli-2 and gli-3 defective mutants and Shh knockout mice ([Chiang, 1996]) showed different defects in rib development. At dpc 14.5 and 15.5 staining was observed in the mesenchyme surrounding the developing tracheae (FIG. 2G). Like Su(fu), Shh and Ptc ([Bellusci, 1997]), are expressed in the lung mesenchyme. In transgenic mice overexpressing Shh in the lung an increase in the mesenchymal mass at the expense of the airway epithelium was observed ([Bellusci, 1997]) while in Shh knockout mice the tracheae were widened and less mesenchyme was present. Expression of Gli-1, but not Gli-2 and Gli-3, has been shown to be dependent on Shh. While Gli-1 is expressed in the lung through almost the entire developmental period, Gli-2 and Gli-3 expression was found in two stages, the latter stalling at dpc 16.5 ([Grindley, 1997]), one day later than we observed Su(fu) expression. So far, Su(fu) is coexpressed with Shh and different Gli molecules which makes it very probable that Su(fu) is involved in Shh signalling. The vibrissae field was stained from dpc 12.5 and onwards with the vibrissae themselves spared (FIG. 2D). At dpc 14.5 the stainaing of the interfoullicular tissue was restricted to the tip of the snout. Instead, at dpc 15.5 staining of the vibrissae emerged (FIG. 2l). On tissue sections, Ptc-1, Shh and Gli-1 have shown to be expressed during pelagic hair follicle development as well (St-Jaques, 1998). Additionally, the role of PTCH mutations in NBCCs supports the role of this pathway in follicle genesis. In the pelagic hairs however, we could not detect any staining, with a Su(fu) probe. At dpc 9.5 we also observed staining of the heart, the dorsal aorta and the intersegementrary arteries (FIG. 2C). The role of the SHH pathway in the heart development is obvious since Ptc-1 knockout mice were reported to suffer from severe heart malformations. Shh har been shown to be expressed in the mandible at dpc 10.5 and 11.5 only, primarily in the presumptive tooth buds, while Ihh is expressed until dpc 14.5 mainly in the epithelium and to a lesser extend in the mesenchyme. Su(fu) is expressed in the mandible from its origin as mandibular branchial arch at dpc 9.5 (FIGS. 2B, C) and onwards. At dpc 10.5 and 11.5, a strong homogenous staining of the (at this stage unpair) mandibular and maxillar mesenchyme is observed. From dpc 12.5, the tongue which was newly arising from the mandible was stained as well, but from this time the mesenchymal area stained by Su(fu) started to withdraw slowly towards the epithelium lining the oral cavity, the epithelium itself however never being stained. The staining dissappeard from the maxillary mesenchyme completely until dpc 13.5. At the mandible, a thin lining of stain was seen at dpc 14.5, while the tongue was reactive even at dpc 15.5 (FIG. 2H): Mandibular (su(fu) expression could be a response to Ihh signalling. Shh-mediated signalling has shown to be involved in the skull bone development [Kim, 1998]. Accordingly, patients with NBCCS show a high frequency of deformities in the head. We speculate that Ihh and Su(f8) play a similar role in development of the architecture of the mandibular cavity, except the teeth, which have been shown to develop under Shh control. Since at the later stages Su(fu) expression was found at the sites directly adjacent to the IHH secreting epitelium, it could be possible that Su(fu) expression might be induced by IHH. Concerning the toungue however, Su(fu) is to our knowledge the first memeber of the Hh signalling pathway reported to be expressed during the development of this organ. The staining pattern of the limb buds seemed to be separated into two phases. Strong homogenous staining all over the limb buds was observed from their emergence at dpc 9.5 (FIG. 2B) through dpc 11.5. At dpc 12.5, however, only the interdigital mesenchyme of the limbs was reactive (FIG. 2D), at dpc 13.5 through 15.5 the staining was adjacent to the sites of chondrification at the prospective bones of the limbs (FIGS. 2E, J, K). Mo et al. stained embryonic mouse limbs for ant three Gli isoforms by whole mount in situ hybridization. At dpc 10 out results congrue with the staining for Gli-2 and Gli-3 where the whole limb bud is reactive in contrast to Bli-1 where only the posterior half of the limb bud is stained. The reaction pattern that we observed with staining for Su(fu) resembled that of staining for Gli-2 where the interdigital mesenchyme was reactive at the border to the condensing mesenchyme while with Gli-3 the entire interdigital and with Gli-1 the condensing mesenchyme was reactive. While the former examples seem to support the hypothesis of Su(fu) as a member of the hedgehog pathway in general, the latter two examples suggest that the action of Su(gu) covers only a pair of the range of this pathway. The expression patterns of Su(fu) suggests that it may be an instrument for tissue-specific modification of hedgehog activity. The expression in the interdigital mesenchyme or in the mandible could result in keeping the space (between the fingers, in the mouth cavity) open and free from growing mesenchyme.

SUFUH Inhibits GLI-1 Transcriptional Activity

Given the pattern of expression during embryogenesis and strong homology to the *Drosophila sufu* gene, we wanted to test the involvement of SUFUH in PTCH-GLI signalling. For this purpose we used transfection assays with the firefly luciferase reporter gene under the control of the human PTCH promoter region. This 4.3 kb promoter region was previously cloned, sequenced and shown to contain two well-conserved GLI consensus sites (Ptc-luc, P. Kogerman, F. Rahnama, E. Lindström, P. G. Zaphiropoulos and R. Toftgard, unpublished results). As shown in FIG, 3A, GLI-1 can activate reporter gene activity from this construct in 293 cells severalfold, whereas SUFUH alone has no effect on promoter activity. However, when cotransfected with GLI-1, SUFUH suppressed the induced level of transcription in a dose-dependent manner (FIG. 3A). To analyze whether the GLI consensus sites could mediate this effect, we constructed a synthetic enhancer consisting of 12 repeated GLI consensus sites fused to the thymidine kinase basic promoter and the luciferase reporter gene (Gli-luc). As shown in FIG. 3B, GLI-1 activates this construct very strongly, whereas, again SUFUH has no effect by itself. However, similarly to the situation with the Ptc-luc reporter, SUFUH strongly suppresses activation of this artificial reporter gene construct by GLI-1 (FIG. 3B).

Since it recently has been determined that the originally-isolated GLI-1 gene contained a potentially activating mutation, we introduced a reverse mutation into the GLI-1 cDNA obtained from Dr. K. Kinzler (Johns Hopkins University, Baltimore, Md.). We demonstrated that in reporter gene assays this plasmid behaved similarly to the clone originally isolated by Kinzler (data not shown). This wild-type (wt) clone was used in all subsequent experiments unless otherwise indicated.

Gli-1 and SUFUH Form a Complex and Colocalize in Cells

These results suggested that GLI-1 and SUFUG function very closely in the signal transduction pathway and raised the possibility that they might associate physically or be in the same macromolecular complex as reported for the fly counterparts. To test this possibility, epitope tagged versions of both GLI-1 and SUFUH were created by fusing a HA-tag to the N-terminus of GLI-1 and a myc-tag to the N-terminus of SUFUH. After confirming their functional activity in the reporter gene assays (data not shown) these constructs were transiently expressed in 293 cells either alone or in combination. As shown in FIG. 4A, HA-GLI-1 was coprecipitated when myc-SUFUH was immunoprecipitated with anti-myc antibody, and conversely, when HA-GLI-1 was immunoprecipitated with anti-HA antibody, myc-SUFUH was also present in the complex.

Using these tagged constructs, the subcellular localizations of SUFUH and both mutated(mut) and wild-type (wt) GLI-1 were determined. As shown in FIG. 4B, SUFUH was present both in the cytoplasm and in the nucleus. Mut GLI-1 was both nuclear and cytoplasmic as well, whereas wt GLI was predominantly cytoplasmic, with some spots of staining seen in the nucleus. When both SUFUH and wt GLI-1 were co-expressed in the same cell, localization of SUFUH was unchanged, whereas the GLI-1 spots in the nucleus disappeared (FIG. 4B). We speculate that the nuclear spots represent GLI-1 complexed with enhance sequences of target genes in "transcriptosomes", and that these complexes might not be formed in the presence of SUFUH resulting in the loss of GLI-1 transcriptional activity as detected in oui reporter gene assays.

The present inventors have identified mouse and human homologs of Drosophila Sufu, a negative regulator of the hedgehog pathway in flies. The expression of su(fu) during embryonic development in mouse suggests important and specific functions in developmental processes in mammals; these functions can now be elucidated directly using the tools of genetics. We also demonstrate that SUFUH associates with GLI-1 and inhibits its transcriptional activity. These results are consistent with and can provide a mechanistic explanation for the genetic data from Drosophila according to which Sufu is an inhibitor in the hedgehog signalling pathway. It was recently proposed that Sufu may interact with Cos-2 on the microtubules in retaining Ci in the cytoplasm and/or directing it towards processing to an inhibitory form. We propose instead that Fu and Su(fu) represent a second independent arm in the pathway that acts alternatively or additionally to Cos-2 in controlling Ci activity (FIG. 5.). This hypothesis is based on the following observations: 1 ) Increased staining with antibodies against the C-terminus of Ci in response to hH can be seen even in Fu negative cells that we now know corresponds to generation of full-length Ci and 2) Fu gets hyperphosphorylated even in Ptc-negative cells in response to Hh (Tom Kornberg, UCSF, personal communication). We have shown that the evolutionary conserved protein SUFUH can associate with GLI-1 and inhibit its transcriptional activity in mammals, possible by modulating its localization and activity in the nucleus. Thus this study contributes to the unravelling of this important oncodevelopmental pathway and to its transfer from the fly to the mammalian system.

What is claimed is:

1. An isolated polypeptide comprising amino acid sequence of SEQ ID NO 2.

2. An antibody which specifically binds to the polypeptide of claim 1.

3. The antibody of claim 2 wherein said antibody is a monoclonal antibody.

4. A kit comprising a container containing the antibody of claim 2.

5. A kit for detecting a protein comprising SEQ ID NO 2, said kit comprising a container containing the antibody of claim 2.

6. A composition comprising the polypeptide according to claim 1, in combination with a pharmaceutically acceptable carrier.

* * * * *